(12) United States Patent
Brackett et al.

(10) Patent No.: US 7,989,632 B2
(45) Date of Patent: Aug. 2, 2011

(54) CRYSTALLINE FORMS OF SOLVATED ILAPRAZOLE

(75) Inventors: John M. Brackett, Kenosha, WI (US); David T. Jonaitis, Lafayette, IN (US); Wei Lai, West Lafayette, IN (US); Jih Hua Liu, Green Oaks, IL (US); Stephan D. Parent, West Lafayette, IN (US)

(73) Assignee: Il Yang Pharmaceutical Company, Ltd., Yongi-Si, Gyeonggi-Do (KR)

( * ) Notice: Subject to any disclaimer, the term of this patent is extended or adjusted under 35 U.S.C. 154(b) by 766 days.

(21) Appl. No.: 11/966,896

(22) Filed: Dec. 28, 2007

(65) Prior Publication Data
US 2008/0200517 A1 Aug. 21, 2008

Related U.S. Application Data

(60) Provisional application No. 60/877,608, filed on Dec. 29, 2006, provisional application No. 60/887,499, filed on Jan. 31, 2007.

(51) Int. Cl.
*C07D 401/12* (2006.01)
(52) U.S. Cl. ................................... 546/273.7
(58) Field of Classification Search ............... 546/273.7; 514/338
See application file for complete search history.

(56) References Cited

U.S. PATENT DOCUMENTS
6,627,646 B2 * 9/2003 Bakale et al. ................. 514/322

FOREIGN PATENT DOCUMENTS
| WO | WO 95/23140 A | 8/1995 |
| WO | WO 2006/099810 A | 9/2006 |
| WO | WO 2006/118534 A | 11/2006 |

OTHER PUBLICATIONS

Kil et al., "Comparison of, etc.," Journal of Autonmic Pharmacology, 2000, 20, 291-296.*
Vippagunta et al., "Crystalline solids", Advanced Drug Delivery Reviews 48 (2001) 3-26.*
Silverman, The Organic Chemistry of Drug Design and Drug Action, NY: Academic Press, Inc. 1993, 72-76.*
Rowland and Tozer. "Clinical Pharmacokinetics, etc.," 1995, p. 123.*
Wilbraham et al. "Organic and biochemistry . . ." p. 250-251 (1985).*
Garattini "Active drug metabolites . . ." Clin. Pharmacokinetics v.10, p. 216-227 (1985).*
CMU Pharmaceutical polymorphism, intenet p. 1-3 (2002) (printout Apr. 3, 2008).*
Singhal et al., "Drug polymorphism, etc., "Advanced drug delivery reviews 56, 335-347 (2004).*
Concise Encyclopedia, NY: Walter de Gruyter Berlin, 1994, 872-873.*
Brittain ed., "Polymorphism, etc.," NY:Marcel Dekker, Inc., 1999, 1-2, 183-226, 235-238.*
Jain et al., "Polymorphism in Pharmacy", Indian Drugs, 1986, 23(6) 315-329.*
Ulicky. Comprehensive Dictionary of Physical Chemistry, NY: Prentice Hall, 1992, p. 21.*
Muzaffar et al., "Polymorphism and Drug Availability, etc.," J of Pharm. (Lahore), 1979, 1(1), 59-66.*
U.S. Pharmacopia #23, National Formulary #18, 1995, 1843-1844.*
Caira, "Crystalline Polymorphism, etc.," Topics in Current Chemistry, 198, Springer Verlag Berlin Heidelberg 1998, 163-208.*
Doelker, english translation of S.T.P, Pratiques (1999), 9(5), 399-409, pp. 1033.*
International Search Report for PCT/US2007/089137 dated May 15, 2008.
Kim et al., "IY-81149: Antiulcerative $H^+/K^+$-ATPase Inhibitor," *Drugs of the Future*, 24(6), 618-621, 1999.

* cited by examiner

*Primary Examiner* — Patricia Morris
(74) *Attorney, Agent, or Firm* — Nixon Peabody LLP

(57) ABSTRACT

The invention relates to crystalline forms of various solvates of ilaprazole, 2[[(4-methoxy-3-methyl-2-pyridinyl)-methyl]sulfinyl]-5-(1H-pyrrol-1-yl)1H-Benzimidazole. The invention also relates to a pharmaceutical composition for inhibiting gastric acid secretion comprising crystalline ilaprazole hydrate according to the invention in an amount effective to inhibit gastric acid secretion and a pharmaceutically acceptable carrier. The invention also provides methods of treatment for various acid-related gastrointestinal (GI) disorders.

2 Claims, 21 Drawing Sheets

US 7,989,632 B2

CRYSTALLINE FORMS OF SOLVATED ILAPRAZOLE

PRIORITY STATEMENT

This application claims benefit under 35 U.S.C. §119(e) of U.S. Provisional Application No. 60/877,608, filed Dec. 29, 2006 and U.S. Provisional Application No. 60/887,499, filed Jan. 31, 2007, both of which are herein incorporated by reference in their entirety.

FIELD OF THE INVENTION

This invention relates to ilaprazole, 2[[(4-methoxy-3-methyl-2-pyridinyl)-methyl]sulfinyl]-5-(1H-pyrrol-1-yl)1H-Benzimidazole, a substituted benzimidazole having a chiral sulfur atom. More particularly, the invention relates to crystalline forms of solvated ilaprazole. Ilaprazole is a proton pump inhibitor and is useful in the treatment of various acid-related gastrointestinal disorders.

BACKGROUND OF THE INVENTION

Since their introduction in the late 1980s, proton pump inhibitors have improved the treatment of various acid-related gastrointestinal (GI) disorders, including gastroesophageal reflux disease (GERD), peptic ulcer disease, Zollinger-Ellison Syndrome (ZES), ulcers, and nonsteroidal anti-inflammatory drug (NSAID)-induced gastropathy. GERD encompasses three disease categories: non-erosive reflux disease (NERD), erosive esophagitis, and Barrett's esophagus. ZES is caused by a gastrin-secreting tumor of the pancreas that stimulates the acid-secreting cells of the stomach to maximal activity. Proton pump inhibitors have also be used to treat ulcers such as duodenal, gastric, and NSAID-associated gastric/duodenal ulcers.

As antisecretory drugs, proton pump inhibitors are currently the recommended first line therapy, being viewed as more effective than other treatments. In general, proton pump inhibitors offer superior gastric acid suppression over histamine H2-receptor blockers. The use of proton pump inhibitors by patients who suffer from gastric acid-related disorders is generally believed to have led to an increase in their quality of life, productivity, and overall well being.

Proton pump inhibitors are also used to treat extra-esophageal manifestations of GERD (asthma, hoarseness, chronic cough, non-cardiac chest pain), and with antibiotics for Helicobacter pylori eradication. The goals of GERD management are threefold: prompt and sustained symptom control, healing of the injured esophageal mucosa and prevention of GERD-related complications (including stricture formation, Barrett's esophagus, and/or adenocarcinoma). Pharmacological therapy with proton pump inhibitors forms the basis of both acute and long-term management of GERD. Proton pump inhibitors provide effective relief of symptoms and healing of the esophagitis, as well as sustaining long-term remission.

Although therapeutic efficacy is the primary concern for a therapeutic agent, the solid-state form, as well as the salt form of a drug candidate, can be important to its development. Each solid state form (crystalline or amorphous) of a drug candidate can have different physical and chemical properties, for example, solubility, stability, or the ability to be reproduced. These properties can impact the ultimate pharmaceutical dosage form, the optimization of manufacturing processes, and absorption in the body. Moreover, finding the most adequate form for further drug development, can reduce the term and the cost of that development.

Obtaining substantially pure crystalline, amorphous or even other non-crystalline forms is extremely useful in drug development. It permits better characterization of the drug candidate's chemical and physical properties and thereby allows identification of the form or forms with the desired combination of therapeutic effect and comparative ease of manufacture. The solid state crystalline form may possess more favorable pharmacology than the amorphous form or may be easier to process. It may also possess more storage stability.

The solid state physical properties of a drug candidate may also influence its selection as a pharmaceutical active ingredient and the choice of form for its pharmaceutical composition. One such physical property, for example, is the flowability of the solid, before and after milling. Flowability affects the ease with which the material is handled during processing into a pharmaceutical composition. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate. Another important solid state property of a pharmaceutical compound is its dissolution rate in aqueous fluid. The rate of dissolution of an active ingredient in a patient's gastrointestinal fluid may have therapeutic consequences since it impacts the rate at which an orally-administered active ingredient may reach the patient's bloodstream.

In chemical syntheses of drug candidates, such as ilaprazole, intermediates are prepared and unwanted by-products or impurities can be carried forward from earlier steps. Often filtration, separation, and/or purification steps are introduced to remove unwanted by-products or impurities. Incorporating such steps cannot only increase costs but can decrease the overall yield of the synthesis. Having a crystalline intermediate or a crystalline solvated form of the drug candidate within a multi-step synthesis can address these problems. A crystalline intermediate or a crystalline solvate of a drug candidate provides certain advantages—a high purity intermediate can reduce the need for other purification steps and reduce the cost of the synthetic process. Such crystalline compounds provide a focal point in the synthesis where the desired purity can be achieved before conversion to the actual drug product.

These practical physical properties are influenced by the properties of the particular solid state form of the compound, for example, by the conformation and orientation of molecules in the unit cell of the crystalline compound. A crystalline form often has different thermal behavior characteristics from an amorphous, a non-crystalline form or another polymorphic form. Thermal behavior is measured in the laboratory by such techniques as capillary melting point, thermogravimetric analysis (TG) and differential scanning calorimetry (DSC) and may be used, for example, to distinguish some polymorphic forms from others. A particular solid state form generally possesses distinct crystallographic and spectroscopic properties detectable by powder X-ray diffraction (XRPD), single crystal X-ray crystallography, and infrared spectrometry among other techniques.

SUMMARY OF THE INVENTION

The invention relates to crystalline forms of solvated ilaprazole, 2[[(4-methoxy-3-methyl-2-pyridinyl)-methyl]sulfinyl]-5-(1H-pyrrol-1-yl) 1H-Benzimidazole. As known to those of skill in the art, the crystalline form may be present as an unsolvated crystalline form or, depending on the form, it may be solvated. Forms C, D, G, and K have been uncovered as crystalline solvates of ilaprazole with the solvents 1,4-dioxane, THF, methanol, and water, respectively.

The invention also relates to a pharmaceutical composition for inhibiting gastric acid secretion comprising crystalline racemic ilaprazole hydrate according to the invention in an amount effective to inhibit gastric acid secretion and a pharmaceutically acceptable carrier. The invention also provides methods of treatment for various acid-related gastrointestinal (GI) disorders such as those discussed above.

DETAILED DESCRIPTION OF THE INVENTION

Figure 1:
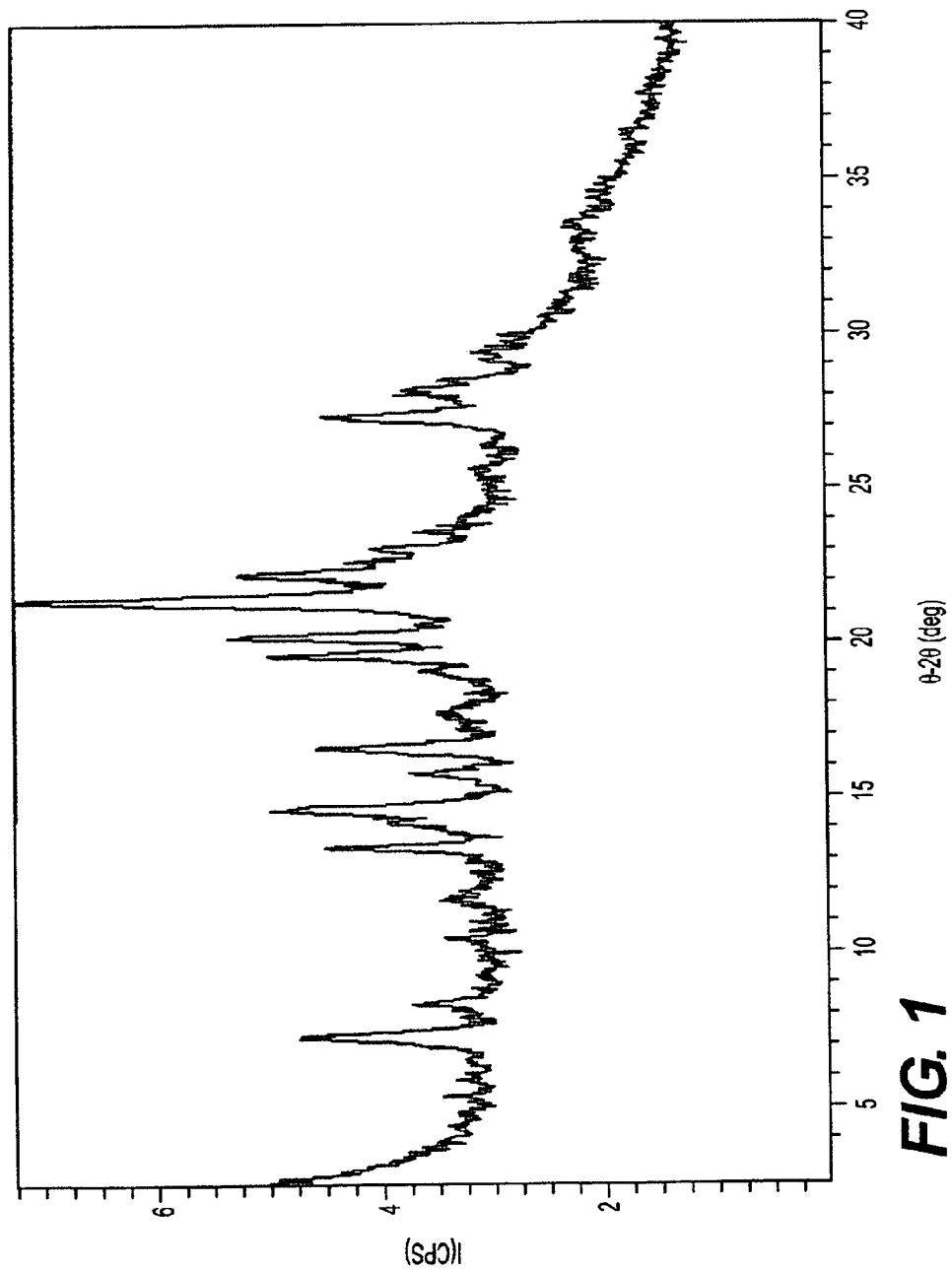
FIG. 1 is the XRPD pattern of crystalline 1,4-dioxane/racemic ilaprazole hemi-solvate, Form C.

Ilaprazole, 2[[(4-methoxy-3-methyl-2-pyridinyl)-methyl]sulfinyl]-5-(1H-pyrrol-1-yl) 1H-Benzimidazole, is a substituted benzimidazole that acts as a proton pump inhibitor. Ilaprazole selectively and irreversibly inhibits gastric acid secretion through inhibition of the hydrogen-potassium adenosine triphosphatase (H+K+-ATPase) (proton pump) mechanism. Inhibition of the proton pump occurs by formation of disulfide covalent bonds with accessible cysteines on the enzyme. Ilaprazole has a prolonged duration of action that persists after their elimination from plasma. See, for example, U.S. Pat. Nos. 5,703,097 and 6,280,773, which are incorporated herein by reference.

Ilaprazole has the empirical formula $C_{19}H_{18}N_4O_2S$ having a molecular weight of 366.44 daltons. Ilaprazole is a chiral molecule and has the following structural formula (I):

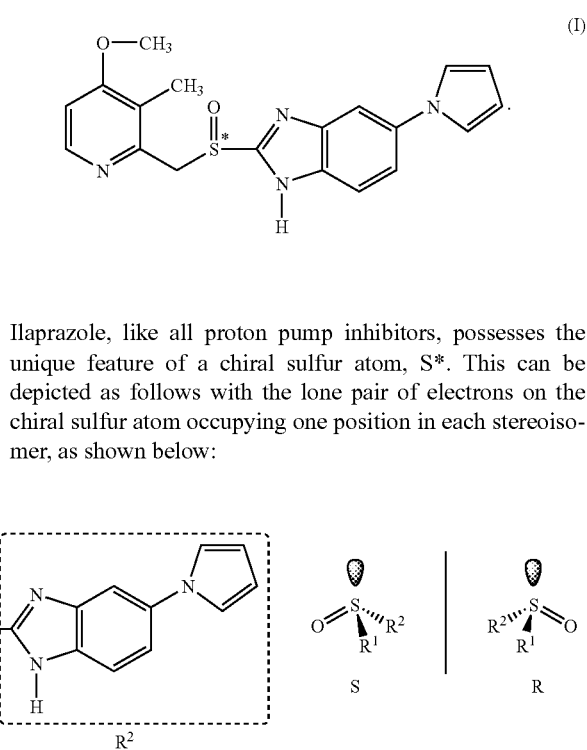

Ilaprazole, like all proton pump inhibitors, possesses the unique feature of a chiral sulfur atom, S*. This can be depicted as follows with the lone pair of electrons on the chiral sulfur atom occupying one position in each stereoisomer, as shown below:

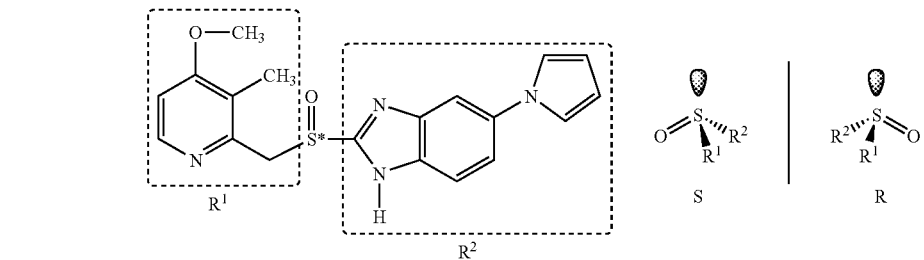

The absolute configuration of (−)-S-ilaprazole was made through single crystal structure determination and is shown below. See Example 7 of co-pending U.S. application Ser. No. 11/966,808 of Brackett et al. entitled, "Solid State Forms of Enantiopure Ilaprazole" filed Dec. 28, 2007, herein incorporated by reference in its entirety.

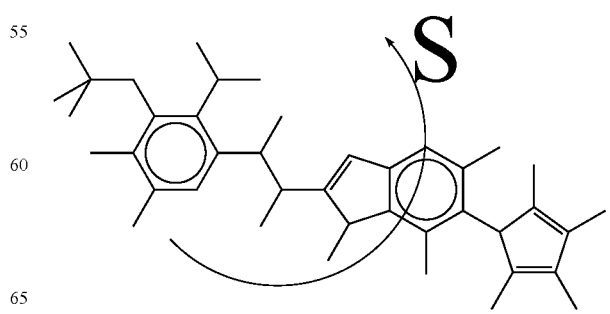

Thus, its complimentary enantiomer is (+)-R-ilaprazole, as shown below.

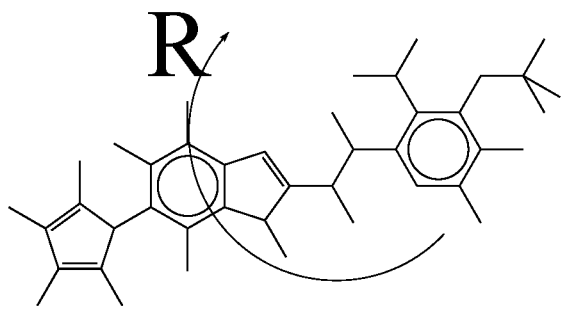

Chiral molecules are well known to chemists. Chiral molecules exist in two enantiomorphic forms that are mirror images of each other. In the same manner that left and right hands are mirror images of each other and cannot be superimposed over each other, enantiomers of chiral molecules cannot be superimposed over each other. The only difference in the molecules is the arrangement of groups connected to the chiral center in three dimensional space. The physical properties of enantiomers are identical to each other with the exception of the rotation of the plane of polarized light. It is this rotation of polarized light that allows one skilled in the art to determine if a chiral material is enantiomerically pure.

In the solid state, pure enantiomeric materials (also known as enantiopure materials) are, by definition, composed of a single enantiomer and can have very different properties compared to racemates. This is particularly true in the crystalline form. Racemates can crystallize as a conglomerate (where the two enantiomers form identical, mirror-image crystals that are the pure enantiomer), a racemic compound (where the two enantiomers coexist and are incorporated into specific locations of the crystal) or a solid solution (where the enantiomers can be located at random sites within the crystal). The solid state can be characterized by various physical properties such as solubility, melting point, x-ray powder diffraction, solid state NMR, Raman, and IR spectroscopy.

The solid state forms of solvated racemic ilaprazole of the invention are designated as Forms C, D, G, and K. Each crystalline form of solvated racemic ilaprazole of the invention is described in the Examples below. The different crystalline forms of solvated racemic ilaprazole can be identified or characterized by comparing their respective spectra, for example their XRPD peaks. The proton NMR spectra are useful in showing that each ilaprazole form is chemically the same as the starting material. Additional data for each crystalline form which may be used to identify each form is presented in the Examples below. Each form disclosed here possesses advantages vis-a-vis the other forms, for example, for a particular formulation or processing, or as an intermediate.

The term "racemic" or "racemate," is defined as a 1:1 mixture of the two enantiomers of ilaprazole regardless of their physical state. A racemic mixture of ilaprazole can be composed of individual crystals which may be the pure enantiomers or ratios of the R and S enantiomers, such as 90/10, 10/90, 86/14, 14/86, 70/30, 30/70, 50/50, as well as other ratios in between these ratios, as long as the bulk enantiomeric composition remains 1:1.

The forms of solvated racemic ilaprazole of the invention are each substantially pure or substantially free of the other crystalline forms or amorphous racemic ilaprazole and other impurities. In this context, "substantially pure" means that the particular form of solvated racemic ilaprazole comprises less than 15% of another crystalline or amorphous form. The purity is preferably less than 10%, more preferably less than 5%, more preferably less than 2%, more preferably less than 1%, and even more preferably less than 0.5%. The term "substantially pure" also means that the form of racemic ilaprazole comprises less than 3% of other impurities, preferably less than 2%, more preferably less than 1%, and even more preferably less than 0.5%.

Crystalline forms of solvated compounds are those where a solvent molecule is contained within the crystalline lattice of the compounds. Solvates may be stoichiometric or non-stoichiometric. Stoichiometric solvates have a fixed ratio of solvent molecules to the molecules of the compound. This is typically due to a bonding interaction between the solvent and the compound molecule. In non-stoichiometric solvates, the solvents is not present in a fixed ratio to the molecules of the compound and often can vary. In a non-stoichiometric solvate, the solvent is often present in the void spaces or channels within the crystalline lattice. Such non-stoichiometric solvates are often called, "channel solvates."

Bulk racemic ilaprazole has now been shown to form crystalline solvates with 1,4-dioxane, THF, methanol, and water. These crystalline solvates, the subject of this invention, include crystalline 1,4-dioxane/racemic ilaprazole solvate, Form C; crystalline THF/racemic ilaprazole hemisolvate, Form D; crystalline methanol/racemic ilaprazole solvate, Form C; and crystalline racemic ilaprazole hydrate, Form K.

While the 1,4-dioxane, THF, and methanol solvates are not suitable for the treatment of various acid-related gastrointestinal (GI) disorders, they are highly pure forms which can be desolvated to yield highly pure ilaprazole, free of other unwanted impurities. For example, the methanol solvate, Form G, when desolvated yields crystalline ilaprazole Form I as described in co-pending U.S. application Ser. No. 11/966,868 of Brackett et al. entitled, "Solid State Forms of Racemic Ilaprazole" filed Dec. 28, 2007, herein incorporated by reference in its entirety. Because hydrates are often used as active pharmaceutical ingredients, Form K is a preferred embodiment of the invention. Solvated forms of compounds are also useful as a point of isolating purified compounds in synthetic processes. A solvate is the least soluble form of the compound in the solvent of solvation. Therefore increasing the yield of the compound and its solvate in a particular solvent may increase the recovery of the compound in that solvent.

Pharmaceutical Compositions and Methods

Ilaprazole is useful for inhibiting gastric acid secretion as well as for providing gastrointestinal cytoprotective effects in mammals, including humans. In a more general sense, ilaprazole may be used for prevention and treatment of gastrointestinal inflammatory diseases in mammals, including e.g. gastritis, gastric ulcer, and duodenal ulcer. As discussed above, such GI disorders include, for example, gastroesophageal reflux disease (GERD), peptic ulcer disease, Zollinger-Ellison Syndrome (ZES), ulcers, and nonsteroidal anti-inflammatory drug (NSAID)-induced gastropathy. Ilaprazole may also be used for prevention and treatment of other gastrointestinal disorders where cytoprotective and/or gastric antisecretory effect is desirable, e.g. in patients with gastrinomas, in patients with acute upper gastrointestinal bleeding, and in patients with a history of chronic and excessive alcohol consumption.

The results of Phase 1 clinical studies conducted with ilaprazole results suggest that at the doses studied, suppression of gastric acid occurs over a 24-hour period. In Phase 2 clinical studies conducted with ilaprazole, the results indicated that ilaprazole at the doses studied provided symptomatic relief for patients with gastric-acid related disorders and promoted rapid healing of acid-related gastric and duodenal ulcers.

Accordingly, the invention relates to a pharmaceutical composition for inhibiting gastric acid secretion comprising crystalline racemic ilaprazole hydrate Form K according to the invention in an amount effective to inhibit gastric acid secretion and a pharmaceutically acceptable carrier. Pharmaceutical compositions are discussed below.

The invention also relates to the treatment of various acid-related gastrointestinal (GI) inflammatory diseases and disorders such as those discussed above and providing gastrointestinal cytoprotection. The invention provides a method for inhibiting gastric acid secretion by administering to mammals crystalline racemic ilaprazole hydrate Form K according to the invention, or a pharmaceutical composition containing it, in an amount sufficient to inhibit gastric acid secretion. The invention also provides a method for the treatment of gastrointestinal inflammatory diseases in mammals by administering to mammals crystalline racemic ilaprazole hydrate Form K according to the invention, or a pharmaceutical composition containing it, in an amount sufficient to treat gastrointestinal inflammatory disease. The invention further provides a method for providing gastrointestinal cytoprotective effects in mammals by administering to mammals crystalline racemic ilaprazole hydrate Form K according to the invention, or a pharmaceutical composition containing it, in an amount sufficient to provide gastrointestinal cytoprotective effects.

The invention relates to pharmaceutical compositions comprising a therapeutically effective amount of crystalline racemic ilaprazole hydrate Form K of the invention and a pharmaceutically acceptable carrier, (also known as a pharmaceutically acceptable excipient). The pharmaceutical composition may also contain a mixture of crystalline form of racemic ilaprazole. As discussed above, crystalline racemic ilaprazole hydrate Form K is suitable for the treatment of various acid-related gastrointestinal (GI) disorders. Pharmaceutical compositions for the treatment of those diseases and disorders contain a therapeutically effective amount of crystalline racemic ilaprazole hydrate Form K of the invention to inhibit gastric secretion as appropriate for treatment of a patient with the particular disease or disorder.

A "therapeutically effective amount of crystalline racemic ilaprazole hydrate Form K to inhibit gastric secretion" (discussed here concerning the pharmaceutical compositions) refers to an amount sufficient to inhibit or reduce gastric secretion and thereby to treat, i.e. to reduce the effects, inhibit or prevent, various acid-related gastrointestinal (GI) disorders and/or provide gastrointestinal cytoprotection. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; and the rate of excretion of the crystalline form of racemic ilaprazole according to the invention; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference.

The absorption of the crystalline forms of racemic ilaprazole can be altered depending on when the subject consumes food in relation to when the dosage is administered. The rate of absorption can also depend on the type of diet consumed, particularly if the diet has a high concentration of fats. These factors, as well as others known to those of skill in the art that can affect the absorption of proton pump inhibitors, can consequently influence the efficacy of the crystalline forms of solvated racemic ilaprazole in inhibiting gastric acid secretion. It has been found that the absorption of the crystalline forms of solvated racemic ilaprazole can be delayed and the bioavailability increased when administered in the fed state or approximately five minutes before a high-fat meal, compared to administration in the fasted state. Administration of the crystalline forms of solvated racemic ilaprazole approximately one hour before a high-fat meal produces results similar to that observed during administration in the fasted state. These findings are consistent with similar studies performed with other tableted formulations of proton pump inhibitors.

A pharmaceutical composition of the invention may be any pharmaceutical Form which contains crystalline racemic ilaprazole hydrate Form K according to the invention. The pharmaceutical composition may be, for example, a tablet, capsule, liquid suspension, injectable, topical, or transdermal. A comprehensive disclosure of suitable formulations (including controlled-release formulations, e.g. delayed release, sustained/extended release, etc.) may be found in U.S. Published Application No. 2006/013868, herein incorporated by reference in its entirety. For injectables and liquid suspensions, those should be formulated such that the crystalline form of solvated racemic ilaprazole is present in the formulated composition.

Depending on the type of pharmaceutical composition, the pharmaceutically acceptable carrier may be chosen from any one or a combination of carriers known in the art. The choice of the pharmaceutically acceptable carrier depends upon the pharmaceutical Form and the desired method of administration to be used. For a pharmaceutical composition of the invention, that is one having crystalline racemic ilaprazole hydrate Form K of the invention, a carrier should be chosen that maintains the crystalline form of racemic ilaprazole hydrate Form K of the invention. In other words, the carrier should not substantially alter the crystalline form of crystalline racemic ilaprazole hydrate Form K of the invention. Nor should the carrier be otherwise incompatible with crystalline racemic ilaprazole hydrate Form K according to the invention, such as by producing any undesirable biological effect or otherwise interacting in a deleterious manner with any other component(s) of the pharmaceutical composition.

The pharmaceutical compositions of the invention are preferably formulated in unit dosage form for ease of administration and uniformity of dosage. A "unit dosage form" refers to a physically discrete unit of therapeutic agent appropriate for the patient to be treated. It will be understood, however, that the total daily dosage of crystalline racemic ilaprazole hydrate Form K of the invention and its pharmaceutical compositions according to the invention will be decided by the attending physician within the scope of sound medical judgment.

It may be desirable to administer the dosage in a composition where the crystalline form of solvated racemic ilaprazole is released from the dosage form as a first and a second dose where each of the first and second dose contain a sufficient amount of the crystalline form of solvated racemic ilaprazole to raise plasma levels to a desired concentration. Suitable formulations to achieve this are disclosed in PCT Published Application No. WO 2006/009602, herein incorporated by reference in its entirety.

Because crystalline racemic ilaprazole hydrate Form K of the invention is more easily maintained during its preparation, solid dosage forms are preferred for the pharmaceutical composition of the invention. Solid dosage forms for oral administration, which includes capsules, tablets, pills, powders, and granules, are particularly preferred. In such solid dosage forms, the active compound is mixed with at least one inert, pharmaceutically acceptable carrier (also known as a pharmaceutically acceptable excipient). The solid dosage form may, for example, include one or more pharmaceutical carriers/excipients as known in the art, including: a) fillers or extenders such as starches, lactose, lactose monohydrate, sucrose, glucose, mannitol, sodium citrate, dicalcium phosphate, and silicic acid; b) binders such as, for example, carboxymethylcellulose, microcrystalline cellulose, alginates, gelatin, polyvinylpyrrolidinone, sucrose, and acacia; c) humectants such as glycerol; d) disintegrating agents such as agar, calcium carbonate, potato or tapioca starch, alginic acid, certain silicates, sodium starch glycolate, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; i) lubricants such as talc, calcium stearate, magnesium stearate, magnesium hydroxide, solid polyethylene glycols, sodium lauryl sulfate; and j) glidants such as colloidal silicon dioxide. The solid dosage forms may also comprise buffering agents. They may optionally contain opacifying agents and can also be of a composition that they release the active ingredient(s) only, or preferentially, in a certain part of the intestinal tract, optionally, in a delayed manner. Remington's Pharmaceutical Sciences, Sixteenth Edition, E. W. Martin (Mack Publishing Co., Easton, Pa., 1980), herein incorporated by reference in its entirety, discloses various carriers used in formulating pharmaceutical compositions and known techniques for the preparation thereof Solid dosage forms of pharmaceutical compositions of the invention can also be prepared with coatings and shells such as enteric coatings and other coatings well known in the pharmaceutical formulating art, including formulations and coatings designed to provide for extended release of the active pharmaceutical ingredient (API). For example, U.S. Pat. No. 6,605,303, incorporated herein by reference, describes oral extended release formulations for the proton pump inhibitor omeprazole. Accordingly, the solid dosage form may be an extended or delayed release formulation. An exemplary delayed-release tablet formulation is described in Example 8 of U.S. application Ser. No. 11/966,868.

Crystalline racemic ilaprazole hydrate Form K of the invention can also be in a solid micro-encapsulated form with one or more carriers as discussed above. Microencapsulated forms of crystalline racemic ilaprazole hydrate Form K of the invention may also be used in soft and hard-filled gelatin capsules with carriers such as lactose or milk sugar as well as high molecular weight polyethylene glycols and the like.

The invention also provides methods for the treatment of the GI disorders discussed above. Crystalline racemic ilaprazole hydrate Form K and pharmaceutical compositions containing it may, according to the invention, be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this invention can be administered to humans and other animals orally, rectally, parenterally, intraveneously, intracisternally, intravaginally, intraperitoneally, topically (as by powders, ointments, or drops), bucally, as an oral or nasal spray, or the like, depending on the location and severity of the condition being treated. As discussed above, when administering a pharmaceutical compositions of the invention via one of these routes, the pharmaceutical composition contains racemic ilaprazole hydrate Form K of the invention. Oral administration using tablets or capsules is generally preferred.

In certain embodiments, the crystalline form of racemic ilaprazole hydrate Form K according to the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. For extended release formulations, the dosage may range from about 5 mg to about 80 mg, preferably ranging from about 10 mg to about 50 mg ilaprazole, and more preferably ranging from about 20 mg to about 40 mg.

EXAMPLES

Example 1 describes the preparation of ilaprazole, From A. Examples 2-4 describe the preparation and characterization of four crystalline ilaprazole solvates of the invention, Forms C, D, G, and K. These solid state forms were characterized by various techniques. Each technique is described below.

Differential Scanning Calorimetry (DSC): Analyses were carried out on a TA Instruments differential scanning calorimeter 2920. The instrument was calibrated using indium as the reference material. The sample was placed into an aluminum DSC pan and the weight accurately recorded. The sample cell was equilibrated at 25° C. and heated under a nitrogen purge at a rate of 10° C./min, up to a final temperature of 350° C. Specific heating rates and pan configurations are identified in the comment section above each individual thermogram. Non-crimped (NC) pan configurations were used.

Dynamic Vapor Sorption/Desorption (DVS): Data were collected on a VTI SGA-100 moisture balance system. For sorption isotherms, a sorption range of 5 to 95% relative humidity (RH) and a desorption range of 95 to 5% RH in 10% RH increments were used for analysis. The samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples.

IR Spectroscopy: Infrared spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. An attenuated total reflectance (ATR) accessory (Thunderdome™, Thermo Spectra-Tech), with a germarium (Ge) crystal was used for data acquisition. The spectra represent 256 co-added scans collected at a spectral resolution of 4 $cm^{-1}$. A background data set was acquired with a clean Ge crystal. Log 1/R (R=reflectance) spectra were acquired by taking a ratio of these two data sets against each other. Wavelength calibration was performed using polystyrene.

NMR Analyses: Samples were prepared for NMR spectroscopy as ~5-50 mg solutions in the solvent indicated in examples. The spectra were obtained on an INOVA-400 spectrometer. The spectra were obtained with the acquisition parameters in Table 1.

TABLE 1

$^1$H NMR Acquisition Parameters

| | |
|---|---|
| Solvent: | $CD_2Cl_2$, DMSO-$d_6$ |
| Temperature: | Ambient |
| Spin rate: | 20 Hz |
| Pulse sequence: | s2pul |
| Relaxation delay: | 5 seconds |
| Pulse width: | 7.0-8.4 μseconds |
| Spectral width: | 6400-7000 Hz |
| Scans: | 40 |
| Acquired points: | 32,000-35,000 |
| Data processing: | |
| Line broadening: | 0.2 Hz |

Thermogravimetry (TG): Analyses were carried out on a TA Instruments 2950 thermogravimetric analyzer. The calibration standards were nickel and Alumel™. Each sample was placed in an aluminum sample pan and inserted into the TG furnace. Samples were started directly from ambient and then heated under a stream of nitrogen at a heating rate of 10° C./min, up to a final temperature of 350° C.

Raman Spectroscopy: FT-Raman spectra were acquired on an FT-Raman 960 spectrometer (Thermo Nicolet). This spectrometer uses an excitation wavelength of 1064 nm. Approximately 0.5 W of Nd:YVO4 laser power was used to irradiate the sample. The Raman spectra were measured with an indium gallium arsenide (InGaAs) detector. The samples were prepared for analysis by placing the sample into a capillary. A total of 256 sample scans were collected from 3600-100 $cm^{-1}$ at a spectral resolution of 4 $cm^{-1}$, using Happ-Genzel apodization. Wavelength calibration was performed using sulfur and cyclohexane.

X-Ray Powder Diffraction (XRPD): XRPD patterns were obtained using an Inel XRG-3000 diffractometer, equipped with a curved position-sensitive detector with a 2θ range of 120°. Real time data were collected using Cu Kα radiation starting at approximately 4° 2θ at a resolution of 0.03° 2θ. The tube voltage and amperage were set to 40 kV and 30 mA, respectively. Samples were run for 5 or 15 minutes. Patterns are displayed from 2.5 to 40° 2θ to facilitate direct pattern comparisons. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard.

XRPD Peak Picking Methods: Any XRPD files generated from an Inel instrument were converted to Shimadzu .raw file using File Monkey version 3.0.4. The Shimadzu .raw file was processed by the Shimadzu XRD-6000 version 4.1 software to automatically find peak positions. The "peak position" means the maximum intensity of a peaked intensity profile. Parameters used in peak selection are shown with each parameter set of the data. The following processes were used with the Shimadzu XRD-6000 "Basic Process" version 2.6 algorithm: 1) smoothing was done on all patterns; 2) the background was subtracted to find the net, relative intensity of the peaks; and 3) the Cu K alpha2 (1.5444 Å wavelength) peak was subtracted from the pattern at 50% of the Cu K alpha1 (1.5406 Å) peak intensity for all patterns.

Each table listing XRPD peaks for each form shows peaks selected by the peak picking method described above. The peak positions are reported in degrees 2θ±0.2° 2θ. I/Io is relative intensity. The tables below listing peaks for each form shows peaks that are visually present in the diffractogram. Only those peaks with an I/Io greater than 3 are listed. The peak positions in bold denote the characteristic peak set for each crystalline form. Shaded entries denote characteristic peak sets with a relative intensity greater than or equal to 10.

Example 1

Preparation of Crystalline Racemic Ilaprazole, Form A

3% $NH_4OH$/Acetonitrile (MeCN) (6.00 kg, 15.0 parts) was charged to a flask. After adjusting the temperature to 5° C. (2-8° C.), crude Ilaprazole (0.400 kg) was charged and the contents were agitated for 1 hour. The slurry was filtered off and the filter cake rinsed with 3% $NH_4OH$/MeCN (2×0.400 kg, 2×1.00 part).

The filter cake was charged into the flask, followed by 0.5% $NH_4OH$/EtOH (0.200 kg, 0.500 part) and concentrated at 20-25° C. under reduced pressure, until distillation stopped. 0.5% $NH_4OH$/EtOH (1.00 kg, 2.50 parts) was charged to the flask, followed by methylene chloride (2.40 kg, 6.00 parts). The resulting solution was concentrated at 20-25° C. under reduced pressure to ca. 1.0 L (2.50 volumes). 0.5% $NH_4OH$/EtOH (1.20 kg, 3.00 parts) was charged and the mixture was concentrated at maximum 20-25° C. under reduced pressure to ca. 1.2 L (3.00 volumes). 0.5% $NH_4OH$/EtOH (0.200 kg, 0.500 part) was charged and the contents were adjusted to 5° C. (2-8° C.) and agitated for 45 minutes. The slurry was filtered off and rinsed with 0.5% $NH_4OH$/EtOH (0.200 kg, 0.500 part), EtOH (0.200 kg, 0.500 part) and MTBE (2×0.200 kg, 2×0.500 part). The filter cake was pull-dried for 2 hours, and further dried under vacuum at maximum temperature of 53° C. for 92 hours. Yield crystalline racemic laprazole, from A:0.338 kg (85%). Particle size: 206

Example 2

Preparation and Characterization of Crystalline 1,4-dioxane/racemic Ilaprazole Hemi-solvate, Form C A solution containing 7 mL of 1,4-dioxane and 10 μL triethylamine (TEA, which is used to stabilize ilaprazole in solution) was saturated with racemic ilaprazole Form A by sonicating with excess solids for approximately 3 minutes. The resulting slurry was filtered through a 0.2 micron nylon filter into a glass vial. The vial was capped and placed into a refrigerator. The resulting white solid was collected by decantation approximately 6 days later and left to air dry at ambient as Form C.

The XRPD pattern of solvated ilaprazole Form C was obtained using an Inel XRG-3000 diffractometer. The data processing conditions are shown in Table 2. FIG. 1 shows the XRPD pattern for crystalline 1.4-dioxane/racemic ilaprazole hemi-solvate, Form C. Table 3 reports the peaks identified in the XRPD pattern.

TABLE 2

XRPD Data Processing Conditions for Form C

| | |
|---|---|
| Smoothing | [AUTO] |
| smoothing points = | 47 |
| B.G. Subtraction | [AUTO] |

TABLE 2-continued

XRPD Data Processing Conditions for Form C

| | |
|---|---|
| sampling points = | 57 |
| repeat times = | 30 |
| Ka1-a2 Separate | [MANUAL] |
| Ka1 a2 ratio = | 50.0 (%) |
| Peak Search | [AUTO] |
| differential points = | 31 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 3

XRPD Peak Positions for Form C

| Position (°2θ ± 0.2 °2θ) | I/I$_o$ |
|---|---|
| 7.2 | 34 |
| 8.3 | 10 |
| 10.3 | 4 |
| 11.7 | 8 |
| 13.3 | 23 |
| 14.5 | 42 |
| 15.7 | 13 |
| 16.5 | 30 |
| 17.6 | 12 |
| 18.9 | 12 |
| 19.5 | 39 |
| 20.1 | 48 |
| 21.3 | 100 |
| 22.2 | 56 |
| 22.8 | 32 |
| 23.6 | 17 |
| 24.1 | 12 |
| 25.4 | 13 |
| 26.3 | 10 |
| 27.2 | 45 |
| 28.1 | 33 |
| 29.3 | 19 |
| 29.9 | 12 |
| 31.0 | 5 |
| 32.7 | 6 |
| 33.4 | 8 |
| 34.5 | 5 |

Figure 2:
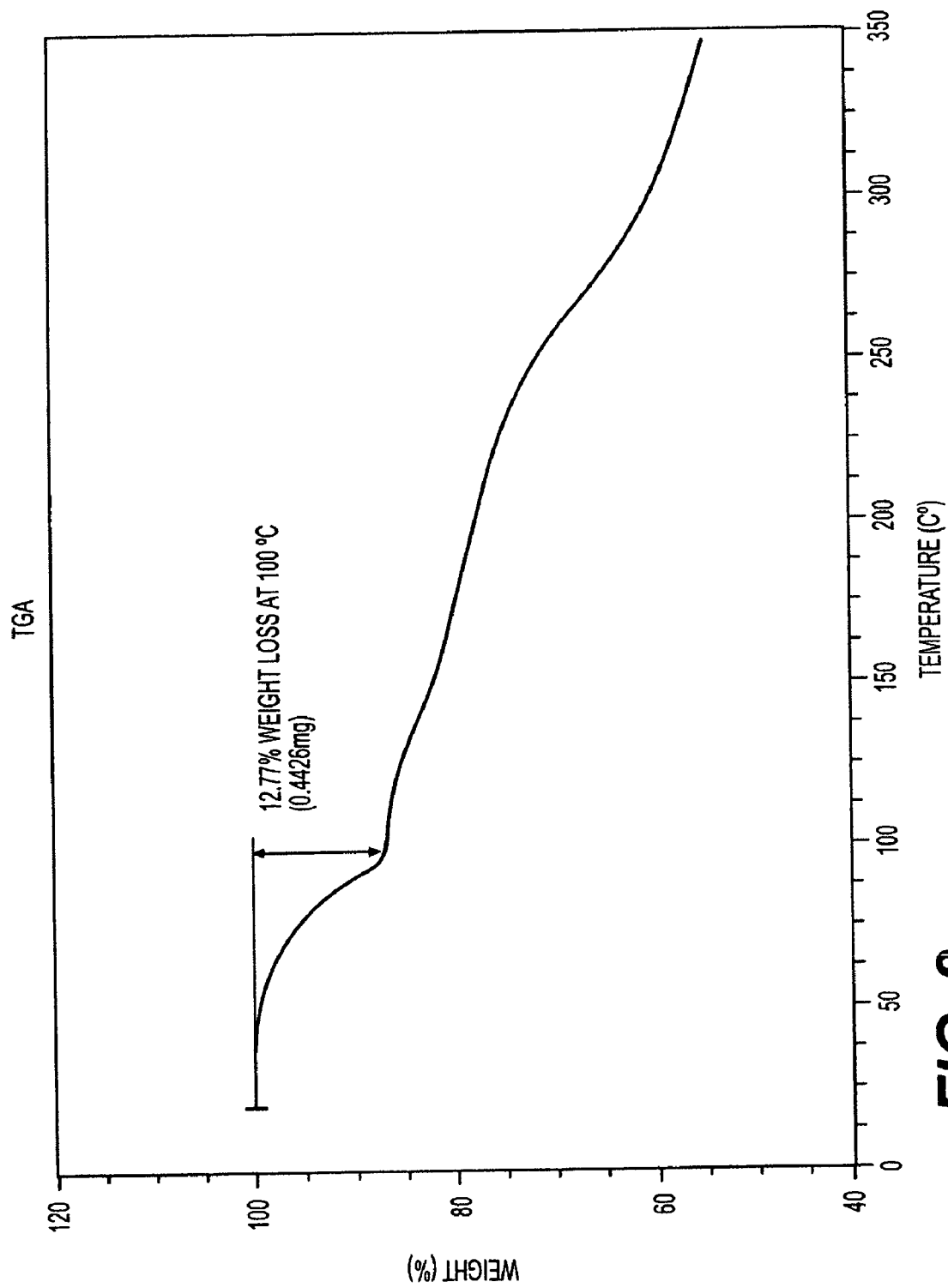
FIG. 2 is the TGA thermogram of crystalline 1,4-dioxane/racemic ilaprazole hemi-solvate, Form C.

FIG. 2 is the TG thermogram of crystalline 1,4-dioxane/racemic ilaprazole hemi-solvate, Form C. The sample showed 12.8% weight loss up to 100° C.

Figure 3:
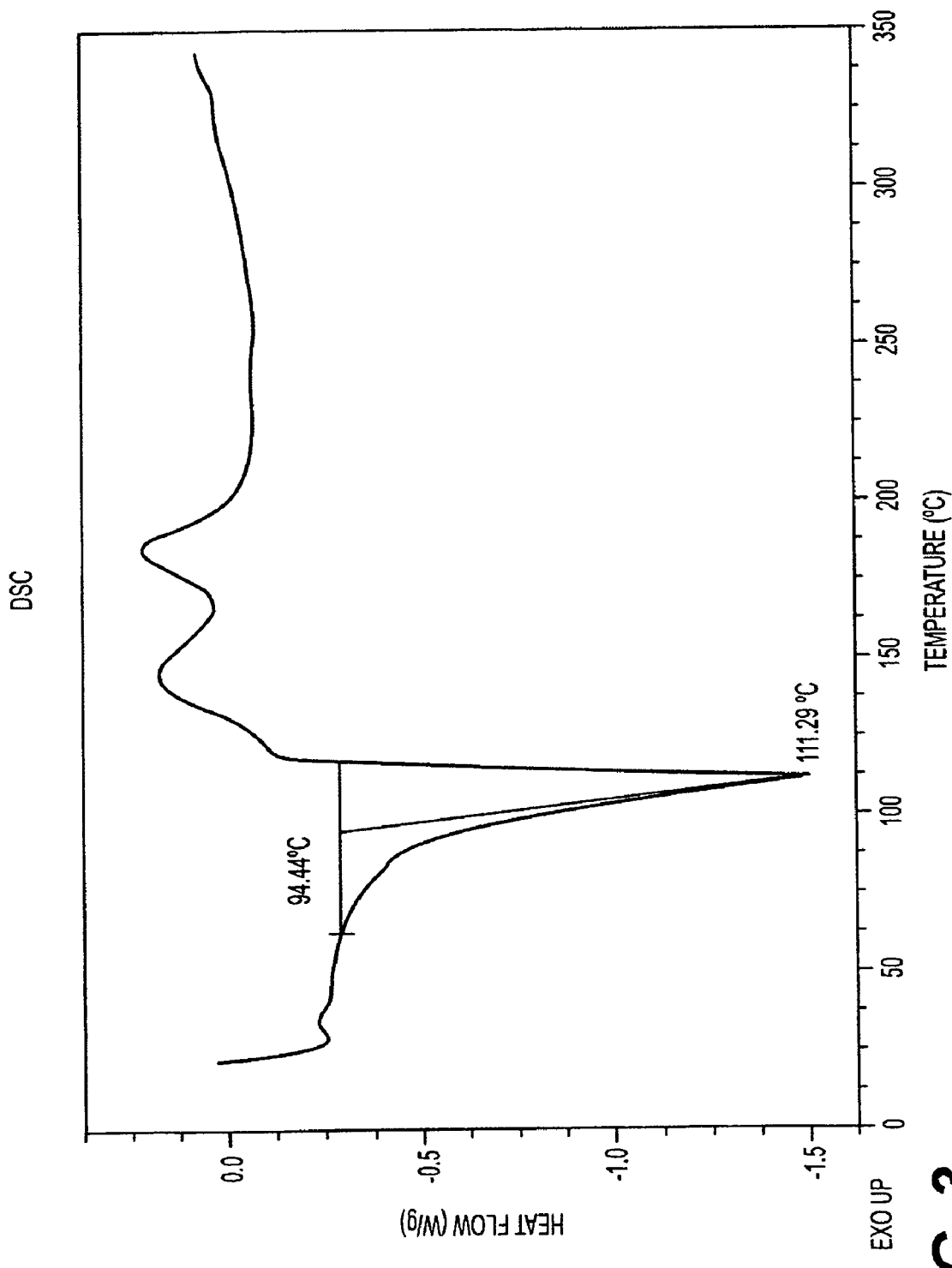
FIG. 3 is the DSC thermogram of crystalline 1,4-dioxane/racemic ilaprazole hemi-solvate, Form C.

FIG. 3 is the DSC thermogram of crystalline 1,4-dioxane/racemic ilaprazole hemi-solvate, Form C. The endotherm onset was at 94° C. (max 111° C.).

Figure 4:
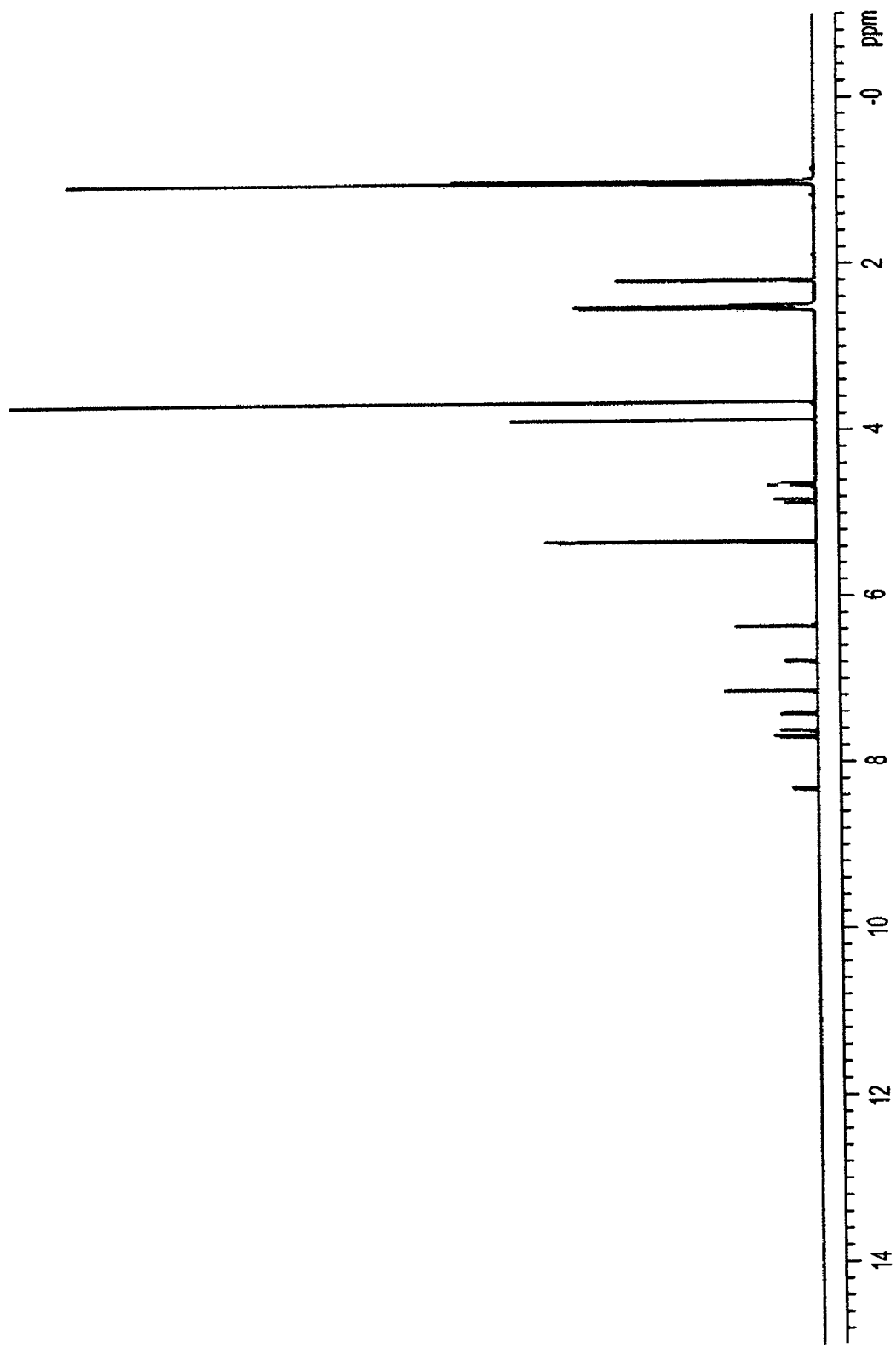
FIG. 4 is the solution state proton NMR spectrum of crystalline 1,4-dioxane/racemic ilaprazole hemi-solvate, Form C.

FIG. 4 is the solution state proton NMR spectrum of crystalline 1,4-dioxane/racemic ilaprazole, Form C, in CD$_2$Cl$_2$. A peak at approximately 3.65 ppm was assigned to 1,4-dioxane and the integration corresponds to ~0.5 moles of 1,4-dioxane. Accordingly, the solution state proton NMR shows that the molar ratio of ilaprazole to 1,4-dioxane in Form C is approximately 1:0.5. Form C is, therefore, considered to be crystalline 1,4-dioxane/racemic ilaprazole hemi-solvate. The peaks in the proton NMR spectrum shown in FIG. 4 are reported in Table 4. Peaks near 5.32 are residual protons in the deuterated solvent—not to ilaprazole. Peaks near 1.0 and 2.5 are due to triethylamine (TEA), which is used to stabilize ilaprazole in solution, and not to ilaprazole.

TABLE 4

Solution $^1$H NMR Peaks for
1,4 Dioxane Ilaprazole Hemi-solvate, Form C.

| PPM |
|---|
| 8.3 |
| 7.7 |
| 7.6 |
| 7.4 |
| 7.1 |
| 6.8 |
| 6.3 |
| 4.8 |
| 4.6 |
| 3.9 |
| 3.6 |
| 2.2 |

Figure 5:
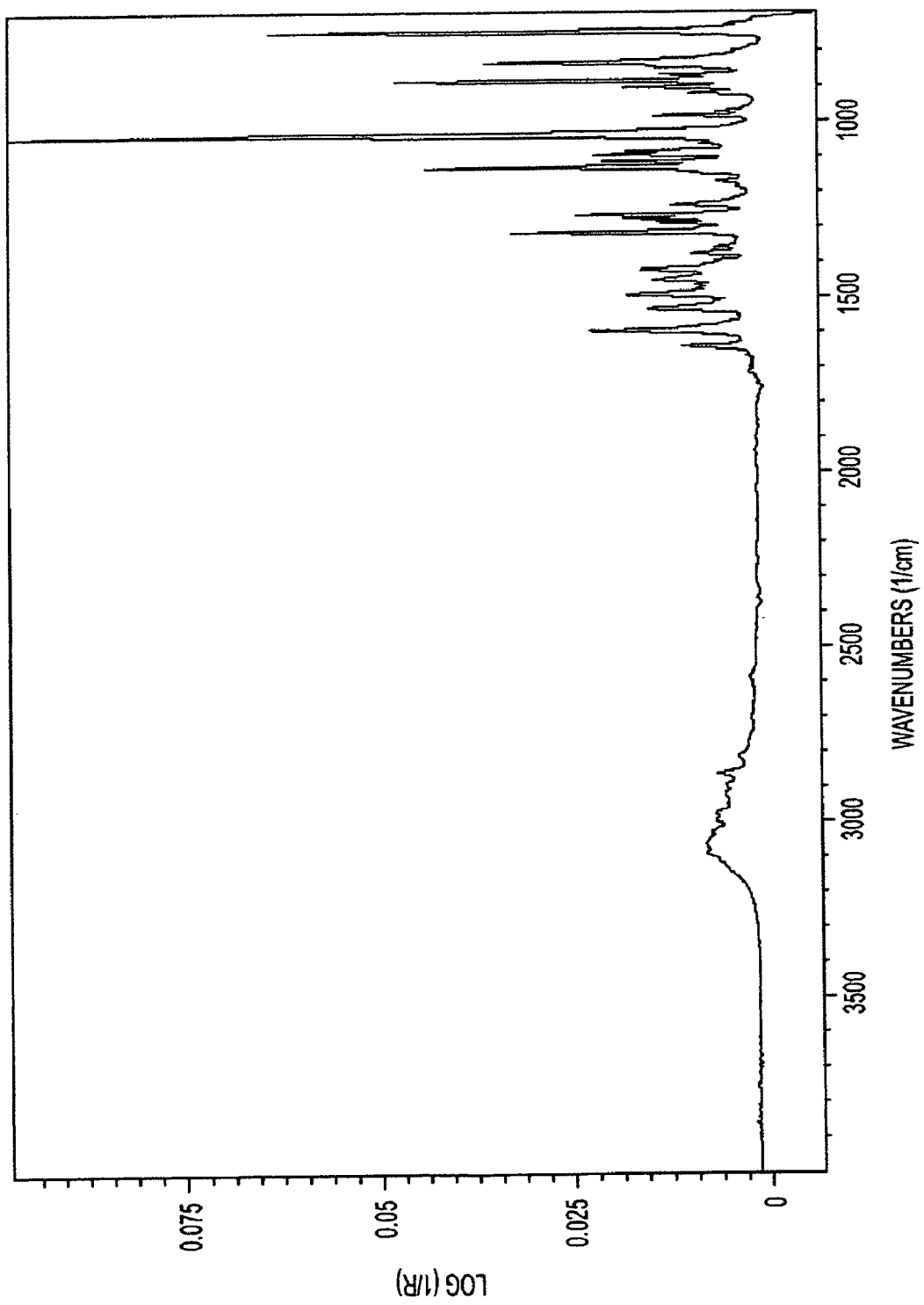
FIG. 5 is the IR spectrum of crystalline 1,4-dioxane/racemic ilaprazole hemi-solvate, Form C.

FIG. 5 is the IR spectrum of crystalline 1,4-dioxane/racemic ilaprazole hemi-solvate, Form C. Table 5 reports the absorbance peaks in the IR spectrum.

TABLE 5

Peaks in IR Spectrum of Solvated Ilaprazole Form C.

| | | | |
|---|---|---|---|
| Position: | 706.8 | Intensity: | 0.0051 |
| Position: | 729.4 | Intensity: | 0.0635 |
| Position: | 782.1 | Intensity: | 0.0043 |
| Position: | 817.4 | Intensity: | 0.0357 |
| Position: | 828.3 | Intensity: | 0.0152 |
| Position: | 851.8 | Intensity: | 0.0133 |
| Position: | 869.0 | Intensity: | 0.0479 |
| Position: | 886.8 | Intensity: | 0.0178 |
| Position: | 903.7 | Intensity: | 0.0097 |
| Position: | 956.2 | Intensity: | 0.0064 |
| Position: | 969.7 | Intensity: | 0.0142 |
| Position: | 1023.8 | Intensity: | 0.0969 |
| Position: | 1047.9 | Intensity: | 0.0085 |
| Position: | 1069.3 | Intensity: | 0.0182 |
| Position: | 1080.1 | Intensity: | 0.0216 |
| Position: | 1098.2 | Intensity: | 0.0211 |
| Position: | 1117.0 | Intensity: | 0.0435 |
| Position: | 1132.3 | Intensity: | 0.0096 |
| Position: | 1155.8 | Intensity: | 0.0063 |
| Position: | 1170.7 | Intensity: | 0.0038 |
| Position: | 1223.0 | Intensity: | 0.0120 |
| Position: | 1251.7 | Intensity: | 0.0238 |
| Position: | 1262.7 | Intensity: | 0.0181 |
| Position: | 1273.4 | Intensity: | 0.0138 |
| Position: | 1302.1 | Intensity: | 0.0324 |
| Position: | 1342.9 | Intensity: | 0.0066 |
| Position: | 1361.2 | Intensity: | 0.0093 |
| Position: | 1382.4 | Intensity: | 0.0066 |
| Position: | 1391.2 | Intensity: | 0.0080 |
| Position: | 1407.2 | Intensity: | 0.0158 |
| Position: | 1437.1 | Intensity: | 0.0141 |
| Position: | 1450.8 | Intensity: | 0.0091 |
| Position: | 1460.4 | Intensity: | 0.0087 |
| Position: | 1479.7 | Intensity: | 0.0176 |
| Position: | 1518.1 | Intensity: | 0.0147 |
| Position: | 1582.0 | Intensity: | 0.0224 |
| Position: | 1626.5 | Intensity: | 0.0107 |
| Position: | 1696.1 | Intensity: | 0.0019 |
| Position: | 2575.8 | Intensity: | 0.0024 |
| Position: | 2803.0 | Intensity: | 0.0040 |
| Position: | 2851.9 | Intensity: | 0.0067 |
| Position: | 2883.6 | Intensity: | 0.0056 |
| Position: | 2911.0 | Intensity: | 0.0057 |
| Position: | 2965.0 | Intensity: | 0.0070 |
| Position: | 2985.2 | Intensity: | 0.0069 |
| Position: | 3052.8 | Intensity: | 0.0081 |
| Position: | 3081.5 | Intensity: | 0.0081 |

Figure 6:
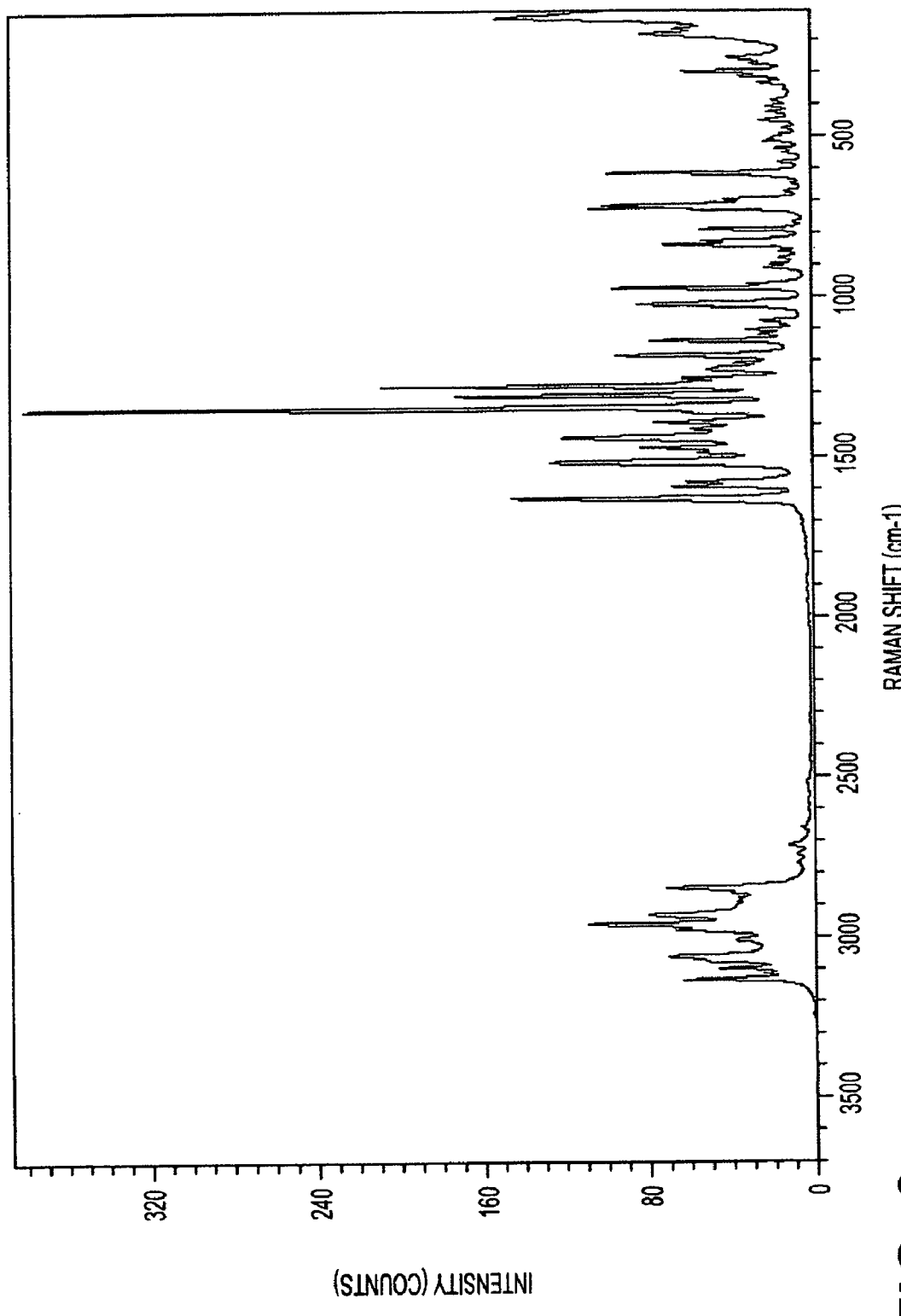
FIG. 6 is the RAMAN spectrum of crystalline 1,4-dioxane/racemic ilaprazole hemi-solvate, Form C.

FIG. 6 is the RAMAN spectrum of crystalline 1,4-dioxane/racemic ilaprazole hemi-solvate, Form C. Table 6 reports the absorbance peaks in the Raman spectrum.

TABLE 6

Peaks in the Raman Spectrum of Solvated Ilaprazole Form C.

| Position: | | Intensity: | |
|---|---|---|---|
| Position: | 416.7 | Intensity: | 14.205 |
| Position: | 443.0 | Intensity: | 17.849 |
| Position: | 466.9 | Intensity: | 6.773 |
| Position: | 486.9 | Intensity: | 8.740 |
| Position: | 498.4 | Intensity: | 12.577 |
| Position: | 507.3 | Intensity: | 16.005 |
| Position: | 531.9 | Intensity: | 11.313 |
| Position: | 543.4 | Intensity: | 7.302 |
| Position: | 574.0 | Intensity: | 9.796 |
| Position: | 607.0 | Intensity: | 92.240 |
| Position: | 640.3 | Intensity: | 3.518 |
| Position: | 665.0 | Intensity: | 7.185 |
| Position: | 690.9 | Intensity: | 36.389 |
| Position: | 707.7 | Intensity: | 95.182 |
| Position: | 717.7 | Intensity: | 101.517 |
| Position: | 758.6 | Intensity: | 4.166 |
| Position: | 782.9 | Intensity: | 48.570 |
| Position: | 821.0 | Intensity: | 47.913 |
| Position: | 831.9 | Intensity: | 68.359 |
| Position: | 852.5 | Intensity: | 11.437 |
| Position: | 873.2 | Intensity: | 11.618 |
| Position: | 892.4 | Intensity: | 16.041 |
| Position: | 904.3 | Intensity: | 18.712 |
| Position: | 955.0 | Intensity: | 26.683 |
| Position: | 967.5 | Intensity: | 92.863 |
| Position: | 1019.2 | Intensity: | 81.462 |
| Position: | 1070.3 | Intensity: | 20.919 |
| Position: | 1080.5 | Intensity: | 12.424 |
| Position: | 1099.0 | Intensity: | 27.385 |
| Position: | 1113.0 | Intensity: | 21.472 |
| Position: | 1134.0 | Intensity: | 73.551 |
| Position: | 1179.6 | Intensity: | 90.482 |
| Position: | 1202.9 | Intensity: | 34.082 |
| Position: | 1224.9 | Intensity: | 46.371 |
| Position: | 1252.5 | Intensity: | 58.963 |
| Position: | 1263.1 | Intensity: | 57.765 |
| Position: | 1274.8 | Intensity: | 203.385 |
| Position: | 1306.0 | Intensity: | 169.771 |
| Position: | 1343.5 | Intensity: | 387.824 |
| Position: | 1391.0 | Intensity: | 73.318 |
| Position: | 1410.1 | Intensity: | 54.936 |
| Position: | 1437.8 | Intensity: | 117.225 |
| Position: | 1469.7 | Intensity: | 79.147 |
| Position: | 1484.9 | Intensity: | 51.522 |
| Position: | 1514.5 | Intensity: | 123.228 |
| Position: | 1577.9 | Intensity: | 57.554 |
| Position: | 1591.7 | Intensity: | 65.022 |
| Position: | 1628.0 | Intensity: | 142.296 |
| Position: | 2520.5 | Intensity: | 1.451 |
| Position: | 2663.9 | Intensity: | 4.214 |
| Position: | 2717.9 | Intensity: | 11.387 |
| Position: | 2745.6 | Intensity: | 7.485 |
| Position: | 2773.2 | Intensity: | 7.385 |
| Position: | 2852.2 | Intensity: | 70.064 |
| Position: | 2867.9 | Intensity: | 39.738 |
| Position: | 2882.9 | Intensity: | 35.868 |
| Position: | 2894.0 | Intensity: | 36.531 |
| Position: | 2936.2 | Intensity: | 79.432 |
| Position: | 2966.1 | Intensity: | 108.294 |
| Position: | 2984.8 | Intensity: | 65.967 |
| Position: | 3017.1 | Intensity: | 38.215 |
| Position: | 3068.2 | Intensity: | 70.018 |
| Position: | 3105.1 | Intensity: | 45.900 |
| Position: | 3122.3 | Intensity: | 25.130 |
| Position: | 3140.0 | Intensity: | 63.509 |

Figure 7:
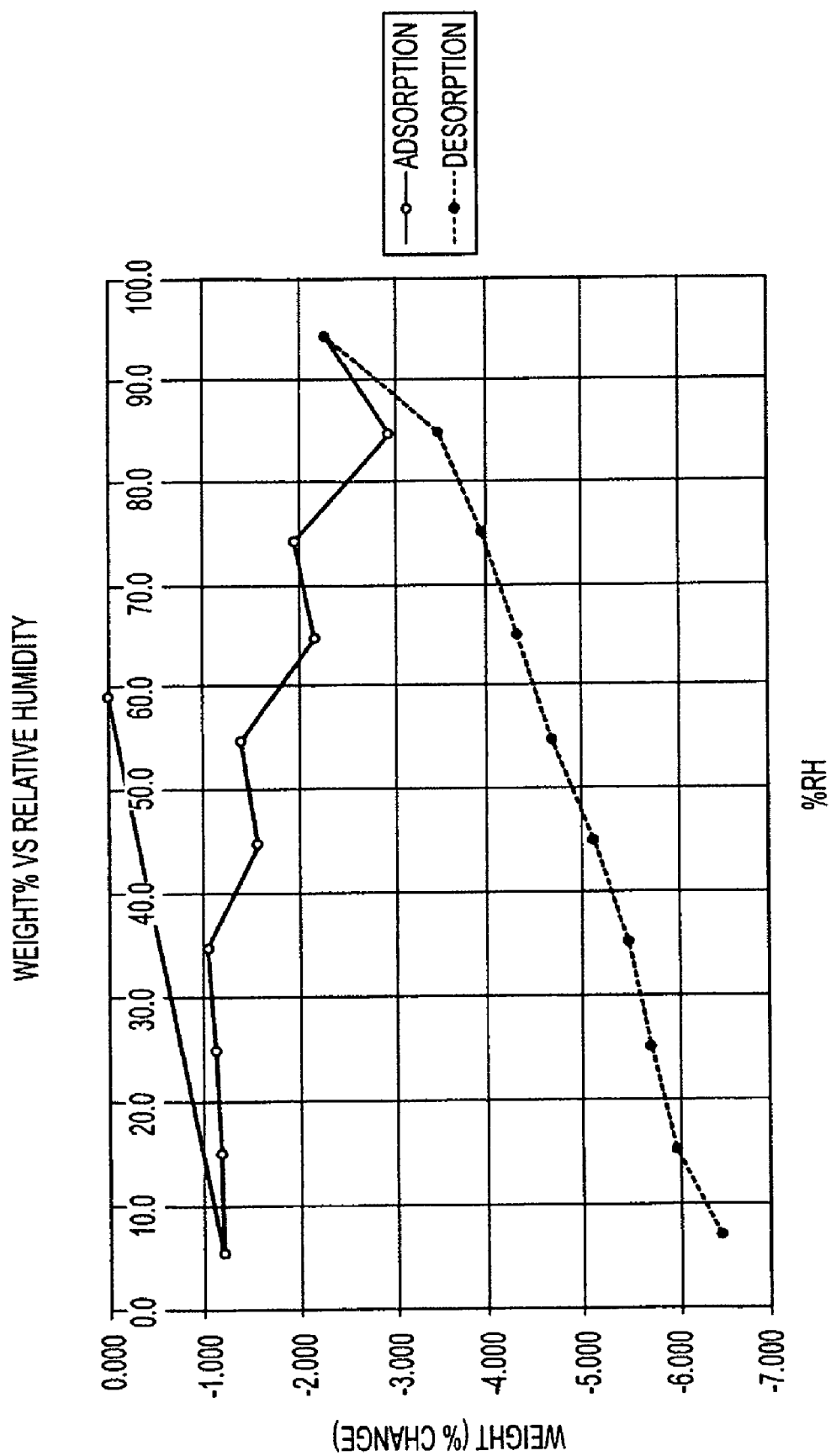
FIG. 7 is the DVS isotherm of crystalline 1,4-dioxane/racemic ilaprazole hemi-solvate, Form C.

FIG. 7 is the DVS isotherm of crystalline 1,4-dioxane/racemic ilaprazole hemi-solvate, Form C. The DVS isotherm shows an approximate 1.2% weight loss at 5% RH, an approximate 1.1% weight loss from 5 to 95% RH and an approximate 4.1% weight loss from 95 to 5% RH.

Example 3

Preparation and Characterization of Crystalline THF/racemic Ilaprazole Hemisolvate, Form D A solution containing 6 mL of THF and 10 µL triethylamine (TEA) was saturated with raceme ilaprazole Form A by sonicating with excess solids for approximately 3 minutes. The resulting slurry was filtered through a 0.2 micron nylon filter into a glass vial. The vial was capped and placed into a refrigerator. After approximately 1 day, the clear solution was moved to the freezer. Solid was noted 3 days later. The sample was placed in dry ice for approximately 3 hours to increase the yield. The white solid was collected by vacuum filtration as Form D.

Figure 8:
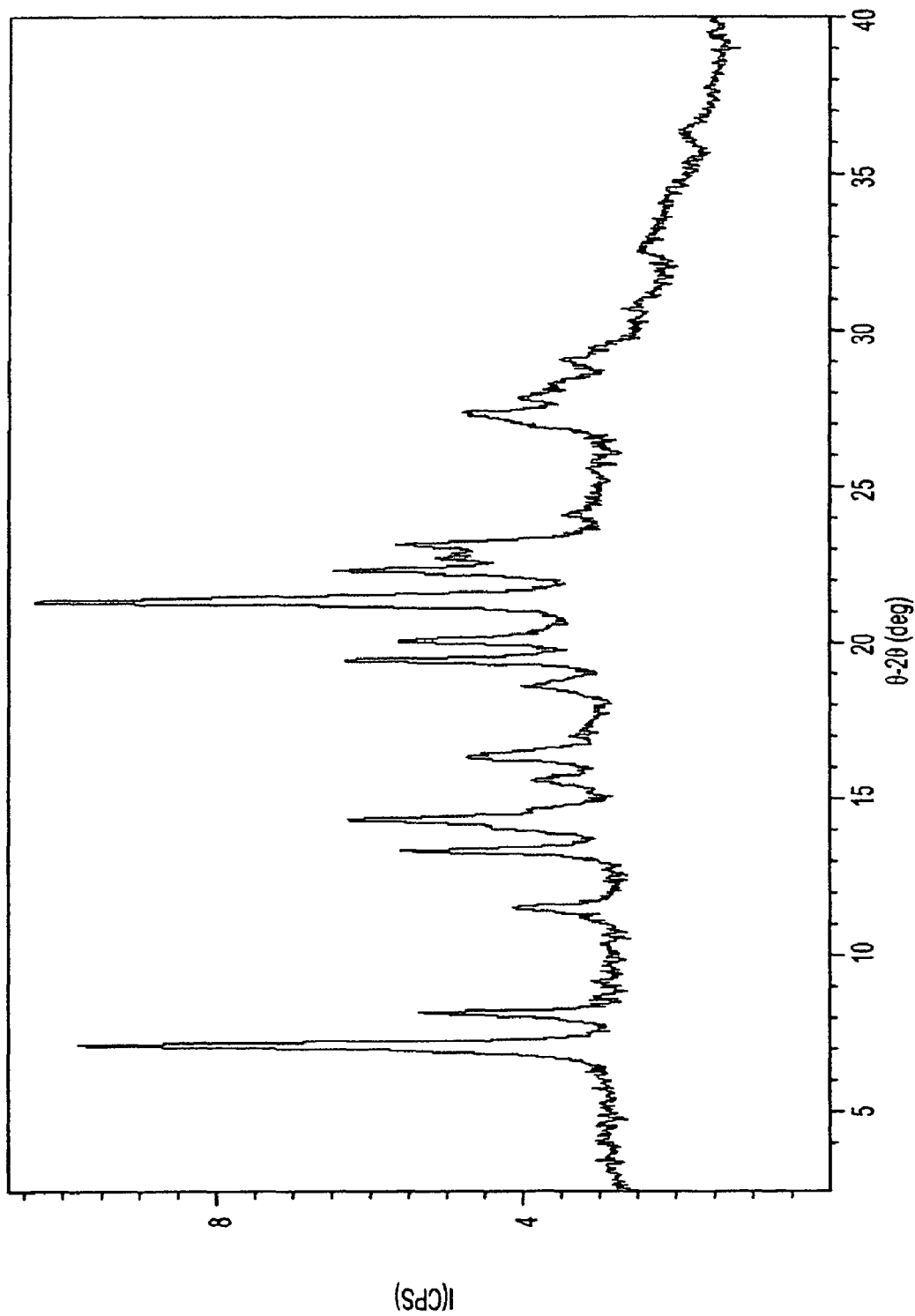
FIG. 8 is the XRPD pattern of crystalline THF/racemic ilaprazole hemi-solvate, Form D.

The XRPD pattern of solvated ilaprazole Form D was obtained using an Inel XRG-300 diffractometer. The measurement conditions are reported in Table 7. FIG. 8 shows the XRPD pattern for crystalline THF/racemic ilaprazole hemisolvate, Form D. Table 8 reports the peaks is identified in the XRPD pattern.

TABLE 7

XRPD Processing Conditions for Form D.

| | |
|---|---|
| Smoothing | [AUTO] |
| smoothing points = | 21 |
| B.G. Subtraction | [AUTO] |
| sampling points = | 23 |
| repeat times = | 30 |
| Ka1-a2 Separate | [MANUAL] |
| Ka1 a2 ratio = | 50.0 (%) |
| Peak Search | [AUTO] |
| differential points = | 17 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 8

XRPD Peak Positions for Form D.

| Position (°2θ ± 0.2 °2θ) | I/I$_o$ |
|---|---|
| 3.3 | 4 |
| 4.3 | 3 |
| 6.2 | 3 |
| 7.1 | 88 |
| 8.2 | 31 |
| 8.7 | 3 |
| 11.1 | 3 |
| 11.5 | 18 |
| 13.1 | 4 |
| 13.4 | 31 |
| 14.0 | 16 |
| 14.3 | 44 |
| 14.8 | 8 |
| 15.6 | 13 |
| 16.4 | 25 |
| 17.0 | 5 |
| 17.3 | 4 |
| 18.6 | 13 |
| 19.5 | 42 |
| 20.1 | 34 |
| 20.5 | 8 |
| 21.4 | 100 |
| 22.3 | 43 |
| 22.8 | 27 |
| 23.2 | 33 |

TABLE 8-continued

XRPD Peak Positions for Form D.

| Position (°2θ ± 0.2 °2θ) | I/I₀ |
|---|---|
| 24.1 | 4 |
| 27.1 | 18 |
| 27.3 | 28 |
| 27.9 | 19 |
| 28.2 | 13 |
| 29.1 | 12 |
| 29.5 | 6 |
| 30.8 | 3 |
| 32.6 | 6 |
| 33.0 | 4 |
| 33.4 | 4 |
| 34.2 | 4 |
| 34.4 | 3 |
| 36.3 | 4 |

Figure 9:
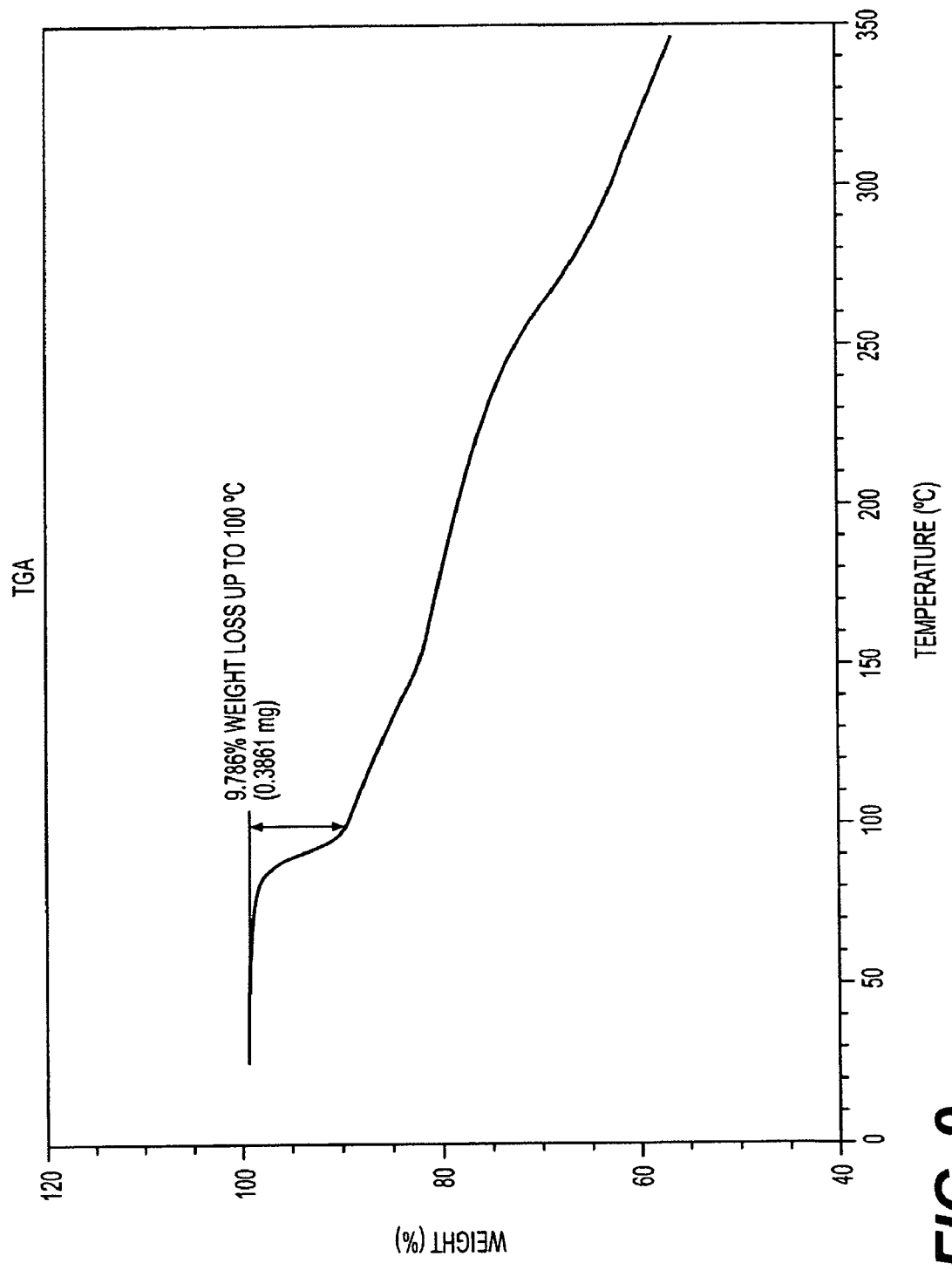
FIG. 9 is the TGA thermogram of crystalline THF/racemic ilaprazole hemi-solvate, Form D.

FIG. 9 is the TG thermogram of crystalline THF/racemic ilaprazole hemisolvate, Form D. The sample showed an approximate 9.8% weight loss up to 100° C.

Figure 10:
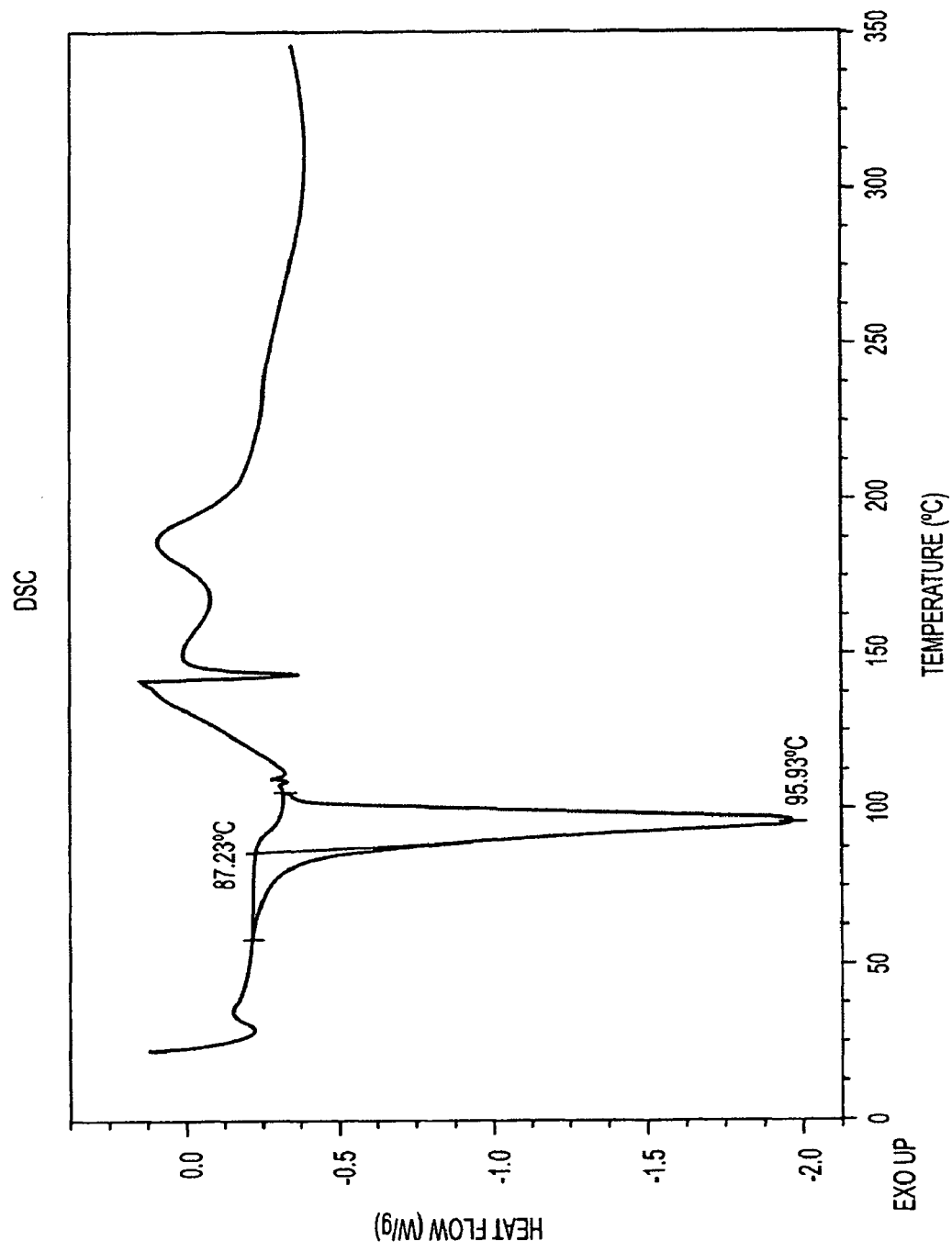
FIG. 10 is the DSC thermogram of crystalline THF/racemic ilaprazole hemi-solvate, Form D.

FIG. 10 is the DSC thermogram of crystalline THF/racemic ilaprazole hemisolvate, Form D. The endotherm onset was at 87° C. (max 96° C.).

Figure 11:
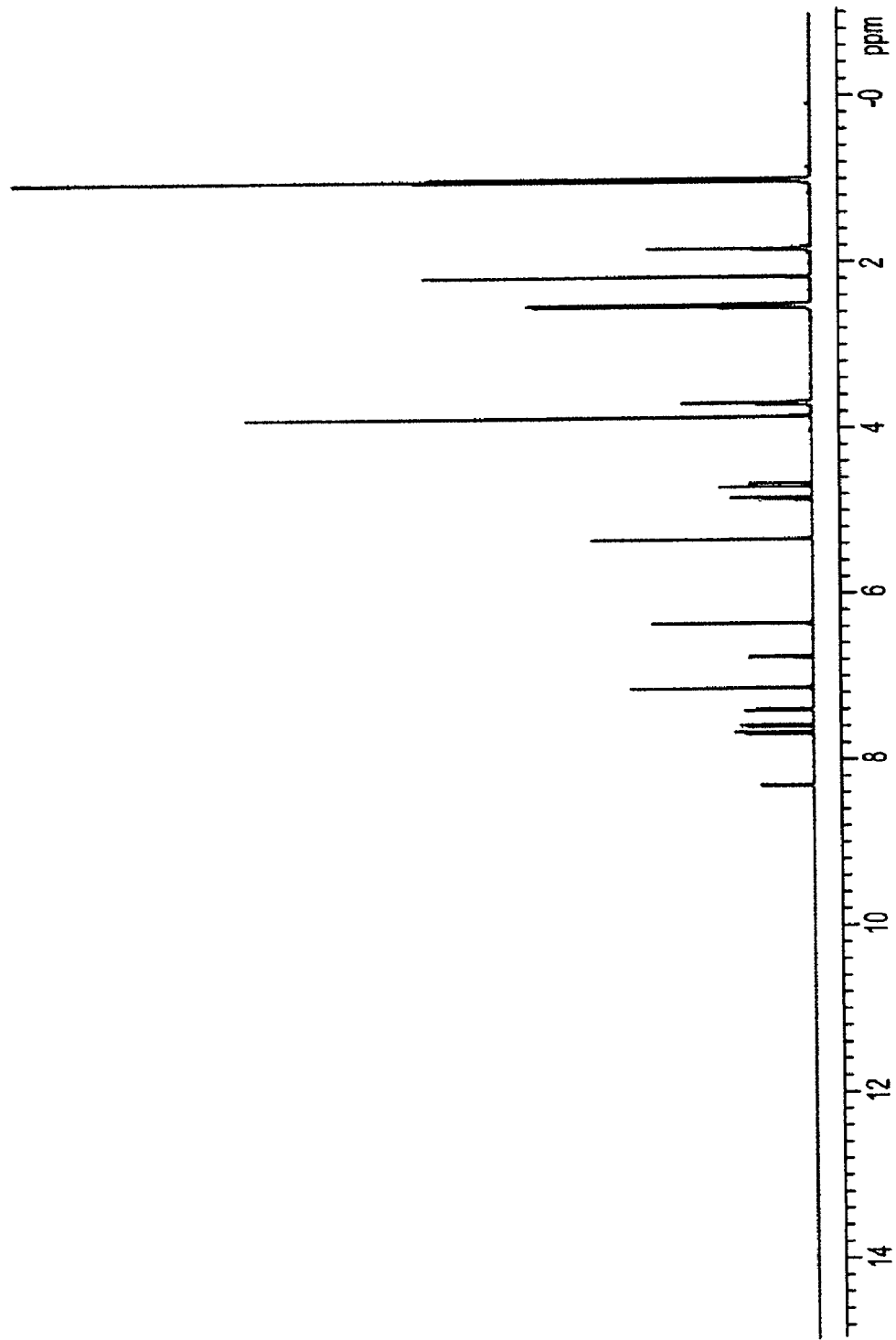
FIG. 11 is the solution state proton NMR Spectrum of crystalline THF/racemic ilaprazole hemi-solvate, Form D.

FIG. 11 is the solution proton NMR Spectrum of crystalline THF/racemic ilaprazole hemisolvate, Form D which shows a ilaprazole to THF ratio of approximately 1:0.5. Peaks at approximately 1.8 ppm and 3.7 ppm were assigned to THF and the integration corresponded to ~0.5 moles of THF. The peaks in the proton NMR spectrum are reported in Table 9. Any peaks near 5.32 ppm are residual protons in the deuterated solvent—not to ilaprazole. Peaks near 1.0 and 2.5 ppm are due to TEA, which is used to stabilize ilaprazole in solution, and not to ilaprazole.

TABLE 9

¹H NMR Peaks for Form D.
PPM

| |
|---|
| 8.3 |
| 7.7 |
| 7.6 |
| 7.4 |
| 7.1 |
| 6.7 |
| 6.3 |
| 4.8 |
| 4.7 |
| 3.8 |
| 3.7 |
| 2.2 |
| 1.8 |

Figure 12:
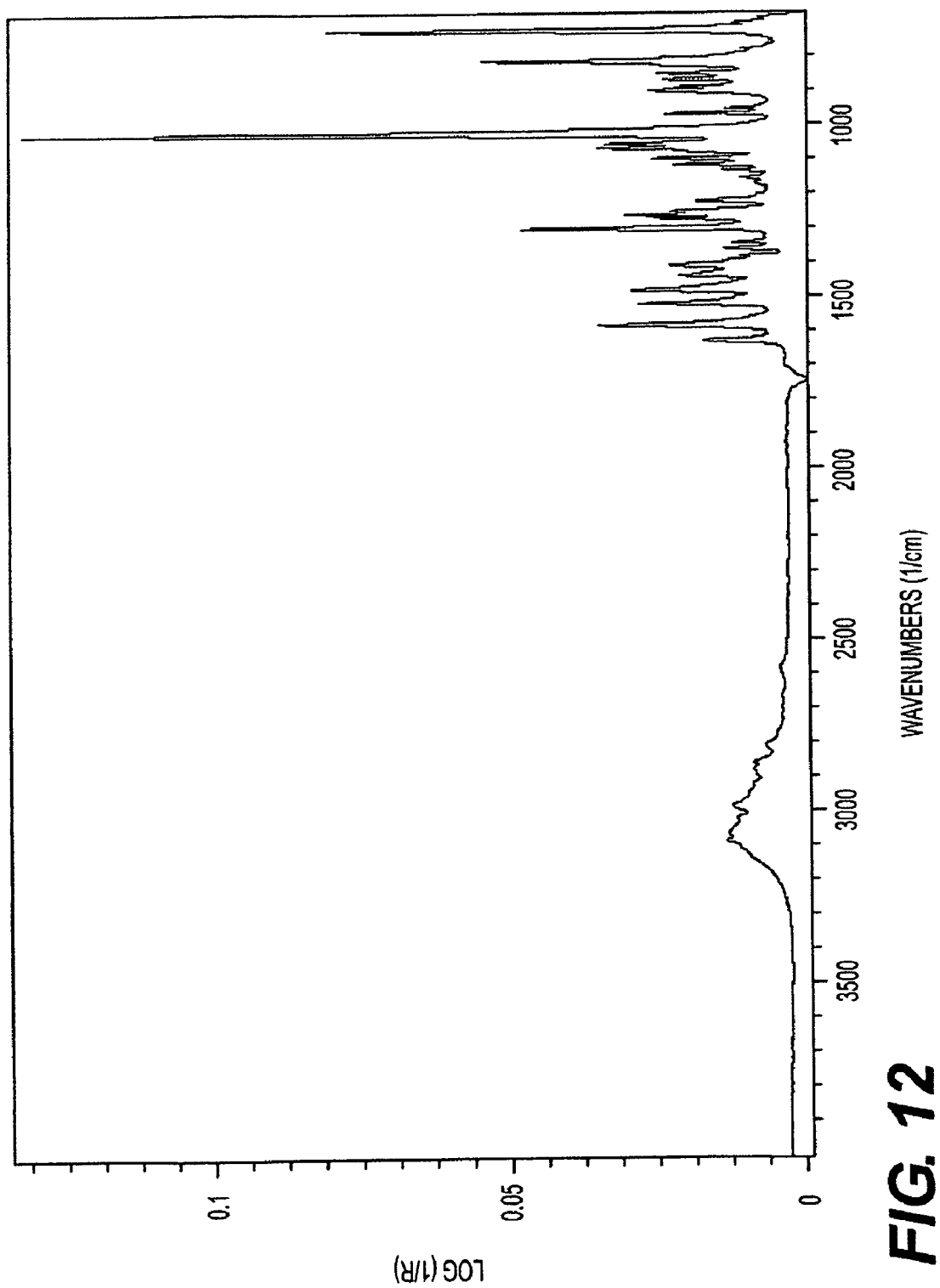
FIG. 12 is the IR spectrum of crystalline THF/racemic ilaprazole hemi-solvate, Form D.

FIG. 12 is the IR spectrum of crystalline THF/racemic ilaprazole hemisolvate, Form D. Table 10 reports the absorbance peaks in the IR spectrum.

TABLE 10

Peaks in IR Spectrum of Form D.

| | | | | |
|---|---|---|---|---|
| Position: | 705.9 | Intensity: | 0.0109 |
| Position: | 726.9 | Intensity: | 0.0791 |
| Position: | 757.8 | Intensity: | 0.0046 |
| Position: | 781.9 | Intensity: | 0.0095 |
| Position: | 815.7 | Intensity: | 0.0532 |
| Position: | 828.3 | Intensity: | 0.0252 |
| Position: | 851.5 | Intensity: | 0.0241 |
| Position: | 869.1 | Intensity: | 0.0227 |
| Position: | 890.6 | Intensity: | 0.0207 |
| Position: | 902.1 | Intensity: | 0.0253 |
| Position: | 954.7 | Intensity: | 0.0123 |
| Position: | 969.6 | Intensity: | 0.0225 |
| Position: | 1026.0 | Intensity: | 0.134 |
| Position: | 1056.3 | Intensity: | 0.0326 |
| Position: | 1068.1 | Intensity: | 0.0340 |
| Position: | 1098.9 | Intensity: | 0.0247 |
| Position: | 1117.5 | Intensity: | 0.0213 |
| Position: | 1134.2 | Intensity | 0.0127 |
| Position: | 1155.4 | Intensity: | 0.0097 |
| Position: | 1170.3 | Intensity: | 0.0073 |
| Position: | 1221.6 | Intensity: | 0.0175 |
| Position: | 1252.1 | Intensity: | 0.0217 |
| Position: | 1262.4 | Intensity: | 0.0300 |
| Position: | 1273.1 | Intensity: | 0.0244 |
| Position: | 1301.2 | Intensity: | 0.0474 |
| Position: | 1342.4 | Intensity: | 0.0112 |
| Position: | 1360.2 | Intensity: | 0.0126 |
| Position: | 1381.8 | Intensity: | 0.0098 |
| Position: | 1406.8 | Intensity: | 0.0219 |
| Position: | 1437.9 | Intensity: | 0.0205 |
| Position: | 1480.2 | Intensity: | 0.0284 |
| Position: | 1517.9 | Intensity: | 0.0270 |
| Position: | 1581.4 | Intensity: | 0.0338 |
| Position: | 1626.4 | Intensity: | 0.0162 |
| Position: | 2578.1 | Intensity: | 0.0034 |
| Position: | 2803.2 | Intensity: | 0.0060 |
| Position: | 2852.8 | Intensity: | 0.0080 |
| Position: | 2872.3 | Intensity: | 0.0081 |
| Position: | 2976.6 | Intensity: | 0.0117 |
| Position: | 3014.1 | Intensity: | 0.0109 |
| Position: | 3062.0 | Intensity: | 0.0122 |
| Position: | 3081.0 | Intensity: | 0.0127 |

Figure 13:
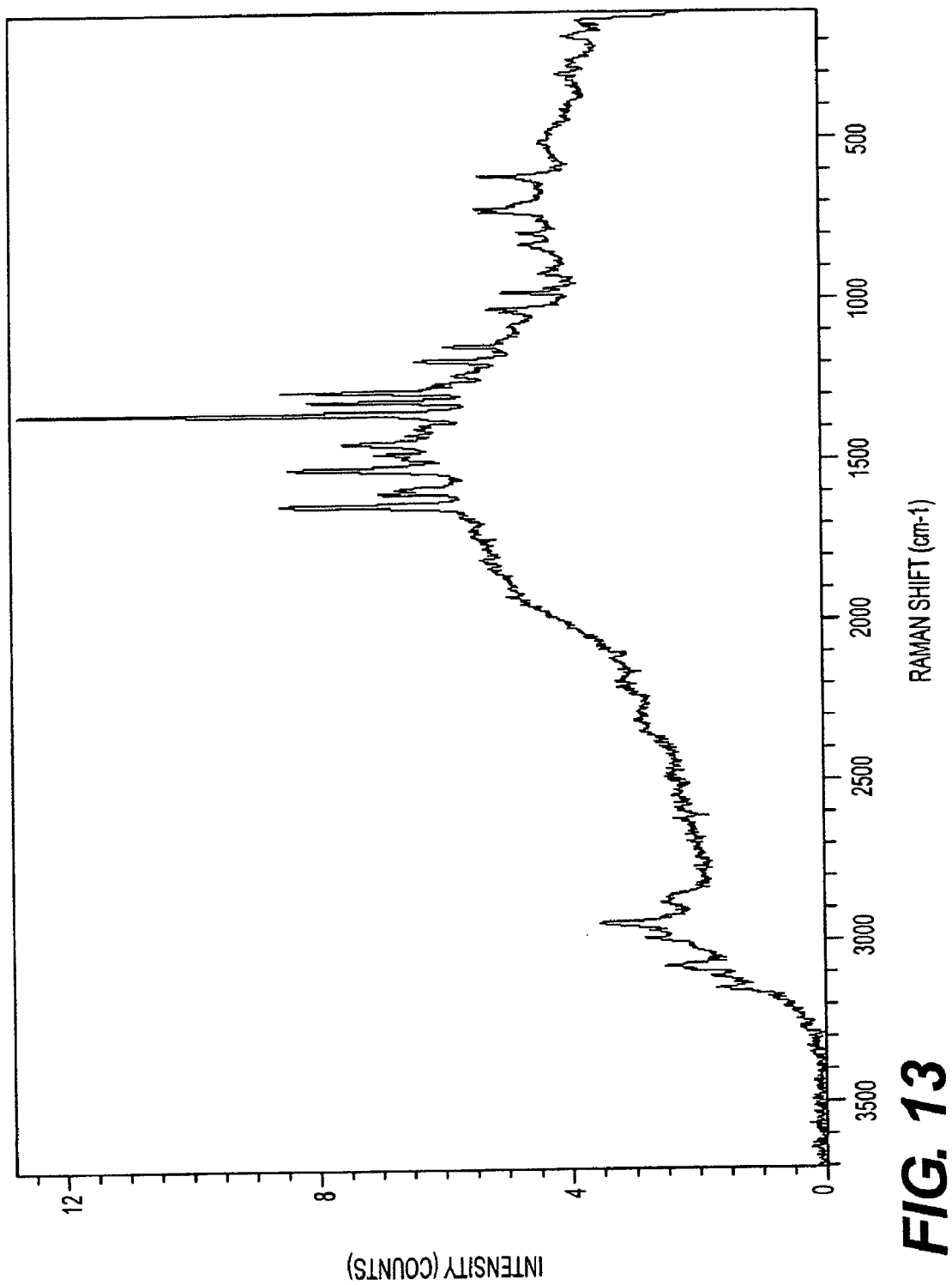
FIG. 13 is the RAMAN spectrum of crystalline THF/racemic ilaprazole hemi-solvate, Form D.

FIG. 13 is the RAMAN spectrum of crystalline THF/racemic ilaprazole hemisolvate, Form D. Table 11 reports the absorbance peaks in the Raman spectrum.

TABLE 11

Peaks in the Raman Spectrum of Form D

| | | | |
|---|---|---|---|
| Position: | 100.2 | Intensity: | 1.737 |
| Position: | 122.2 | Intensity: | 1.095 |
| Position: | 173.2 | Intensity: | 0.756 |
| Position: | 244.7 | Intensity: | 0.385 |
| Position: | 288.6 | Intensity: | 0.534 |
| Position: | 502.7 | Intensity: | 0.517 |
| Position: | 605.6 | Intensity: | 1.312 |
| Position: | 706.5 | Intensity: | 1.207 |
| Position: | 716.8 | Intensity: | 1.109 |
| Position: | 781.2 | Intensity: | 0.483 |
| Position: | 818.0 | Intensity: | 0.571 |
| Position: | 908.4 | Intensity: | 0.578 |
| Position: | 954.0 | Intensity: | 0.496 |
| Position: | 967.1 | Intensity: | 1.118 |
| Position: | 1017.8 | Intensity: | 1.075 |
| Position: | 1028.1 | Intensity: | 0.815 |
| Position: | 1072.2 | Intensity: | 0.465 |
| Position: | 1134.9 | Intensity: | 1.173 |
| Position: | 1178.8 | Intensity: | 1.425 |
| Position: | 1225.8 | Intensity: | 0.601 |
| Position: | 1253.3 | Intensity: | 0.765 |
| Position: | 1275.0 | Intensity: | 3.032 |
| Position: | 1306.0 | Intensity: | 2.499 |
| Position: | 1343.4 | Intensity: | 7.169 |
| Position: | 1391.2 | Intensity: | 0.701 |
| Position: | 1409.8 | Intensity: | 0.818 |
| Position: | 1436.6 | Intensity: | 1.821 |
| Position: | 1468.9 | Intensity: | 1.309 |
| Position: | 1515.2 | Intensity: | 2.686 |
| Position: | 1579.7 | Intensity: | 1.068 |
| Position: | 1591.1 | Intensity: | 1.362 |
| Position: | 1630.2 | Intensity: | 3.040 |

TABLE 11-continued

Peaks in the Raman Spectrum of Form D

| | | | |
|---|---|---|---|
| Position: | 2873.7 | Intensity: | 0.990 |
| Position: | 2936.6 | Intensity: | 2.167 |
| Position: | 2960.7 | Intensity: | 1.503 |
| Position: | 2984.1 | Intensity: | 1.665 |
| Position: | 3069.9 | Intensity: | 1.662 |
| Position: | 3103.1 | Intensity: | 1.073 |
| Position: | 3140.6 | Intensity: | 1.154 |

Figure 14:
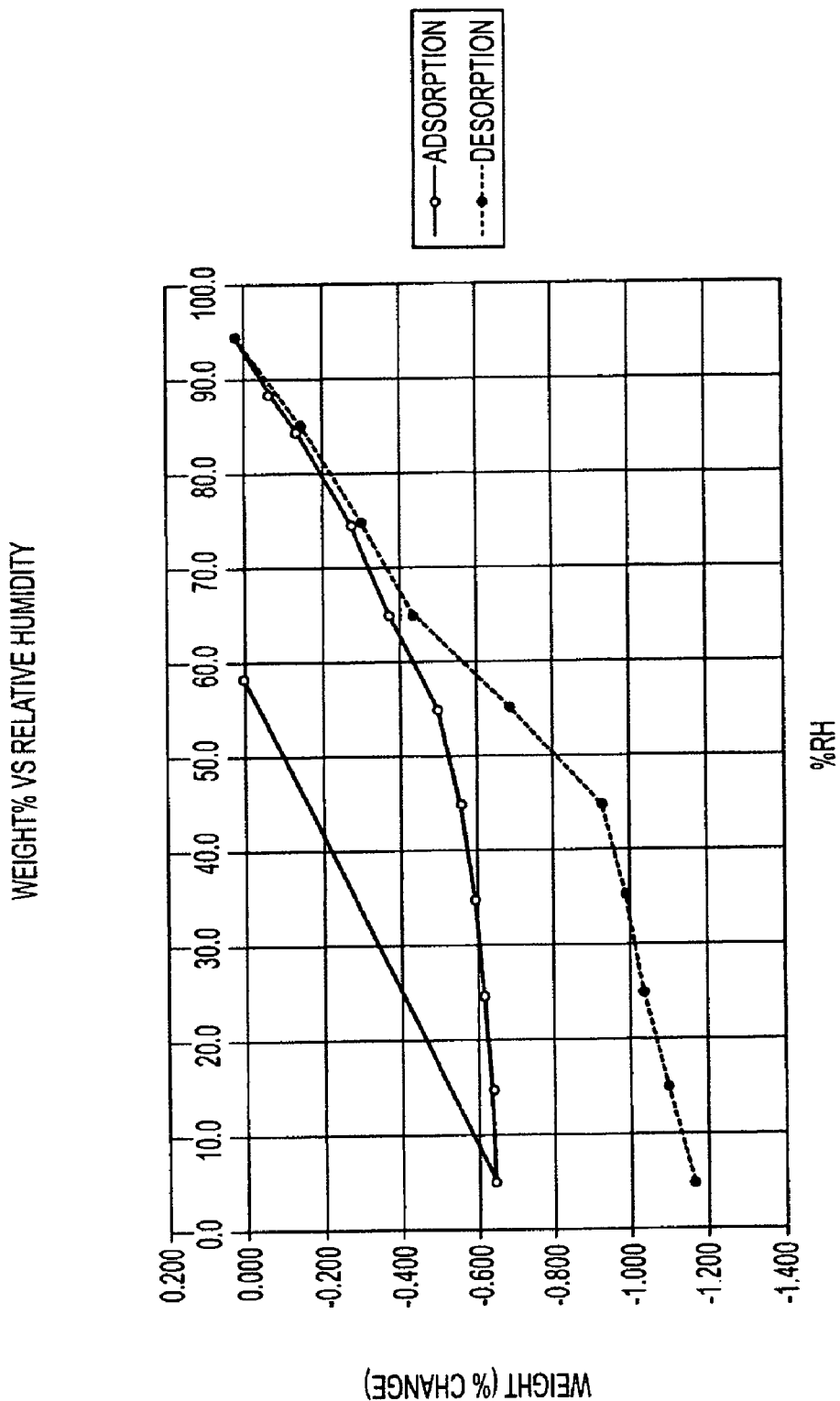
FIG. 14 is the DVS isotherm of crystalline THF/racemic ilaprazole hemi-solvate, Form D.

FIG. 14 is the DVS isotherm of crystalline THF/racemic ilaprazole hemisolvate, Form D. The DVS isotherm shows an approximate 0.6% weight loss at 5% RH, an approximate 0.6% weight gain from 5 to 95% RH, and an approximate 1.2% weight loss from 95 to 5% RH.

Example 4

Preparation and Characterization of Crystalline Methanol/racemic Ilaprazole Solvate, Form G.

A solution containing 3 mL of MeOH and 10 µL triethylamine was saturated with Ilaprazole Form A by sonicating with excess solids for approximately 3 minutes. The resulting slurry was filtered through a 0.2 micron nylon filter into a glass vial. The vial was capped and placed into the freezer. The resulting white solid was collected by vacuum filtration approximately 2 days later as Form G.

Figure 15:
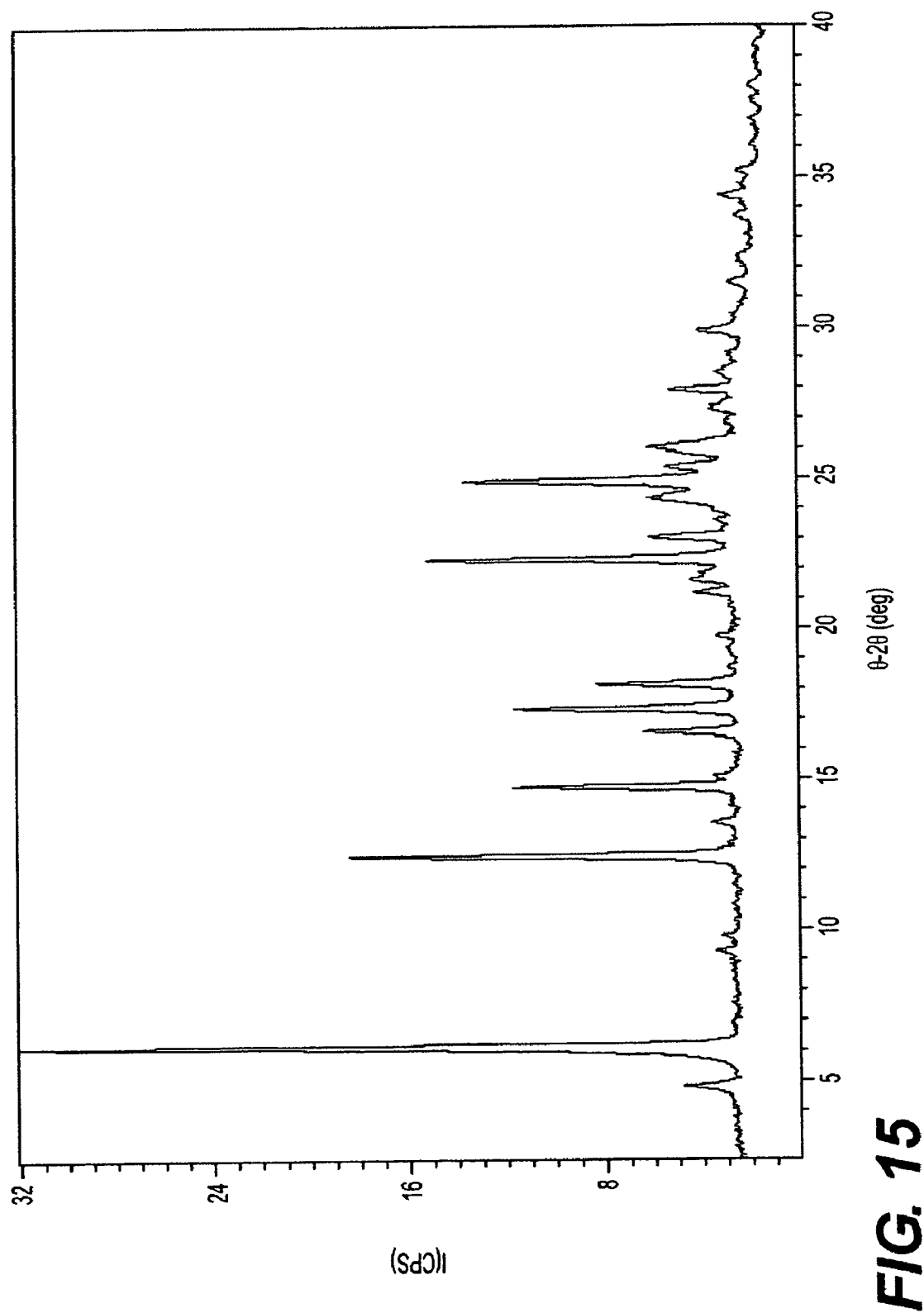
FIG. 15 is the XRPD pattern of crystalline methanol/racemic ilaprazole solvate, Form G.

The XRPD pattern of crystalline methanol/racemic ilaprazole solvate, Form G was obtained using an Inel XRG-3000 diffractometer. The measurement conditions are reported in Table 12. FIG. 15 shows the XRPD pattern for crystalline methanol/racemic ilaprazole solvate, Form G. Table 13 reports the peaks identified in the XRPD pattern.

TABLE 12

XRPD Processing Conditions for Form G.

| | |
|---|---|
| Smoothing | [AUTO] |
| smoothing points = | 9 |
| B.G. Subtraction | [AUTO] |
| sampling points = | 11 |
| repeat times = | 30 |
| Kα1-α2 Separate | [MANUAL] |
| Kα1 α2 ratio = | 50.0 (%) |
| Peak Search | [AUTO] |
| differential points = | 11 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 13

XRPD Peak Positions of Form G

| Position (°2θ ± 0.2 °2θ) | I/I$_o$ |
|---|---|
| 4.9 | 7 |
| 6.2 | 100 |
| 9.4 | 3 |
| 12.5 | 54 |
| 13.6 | 3 |
| 14.8 | 32 |
| 15.1 | 3 |
| 16.6 | 14 |
| 17.2 | 3 |

TABLE 13-continued

XRPD Peak Positions of Form G

| Position (°2θ ± 0.2 °2θ) | I/I$_o$ |
|---|---|
| 17.4 | 33 |
| 18.2 | 21 |
| 19.8 | 3 |
| 21.2 | 5 |
| 21.6 | 6 |
| 21.9 | 4 |
| 22.3 | 45 |
| 23.0 | 12 |
| 24.3 | 11 |
| 24.5 | 8 |
| 24.9 | 38 |
| 25.4 | 9 |
| 26.0 | 11 |
| 27.3 | 4 |
| 27.4 | 3 |
| 27.9 | 10 |
| 29.9 | 7 |
| 31.5 | 3 |
| 34.4 | 5 |
| 35.2 | 3 |

Figure 16:
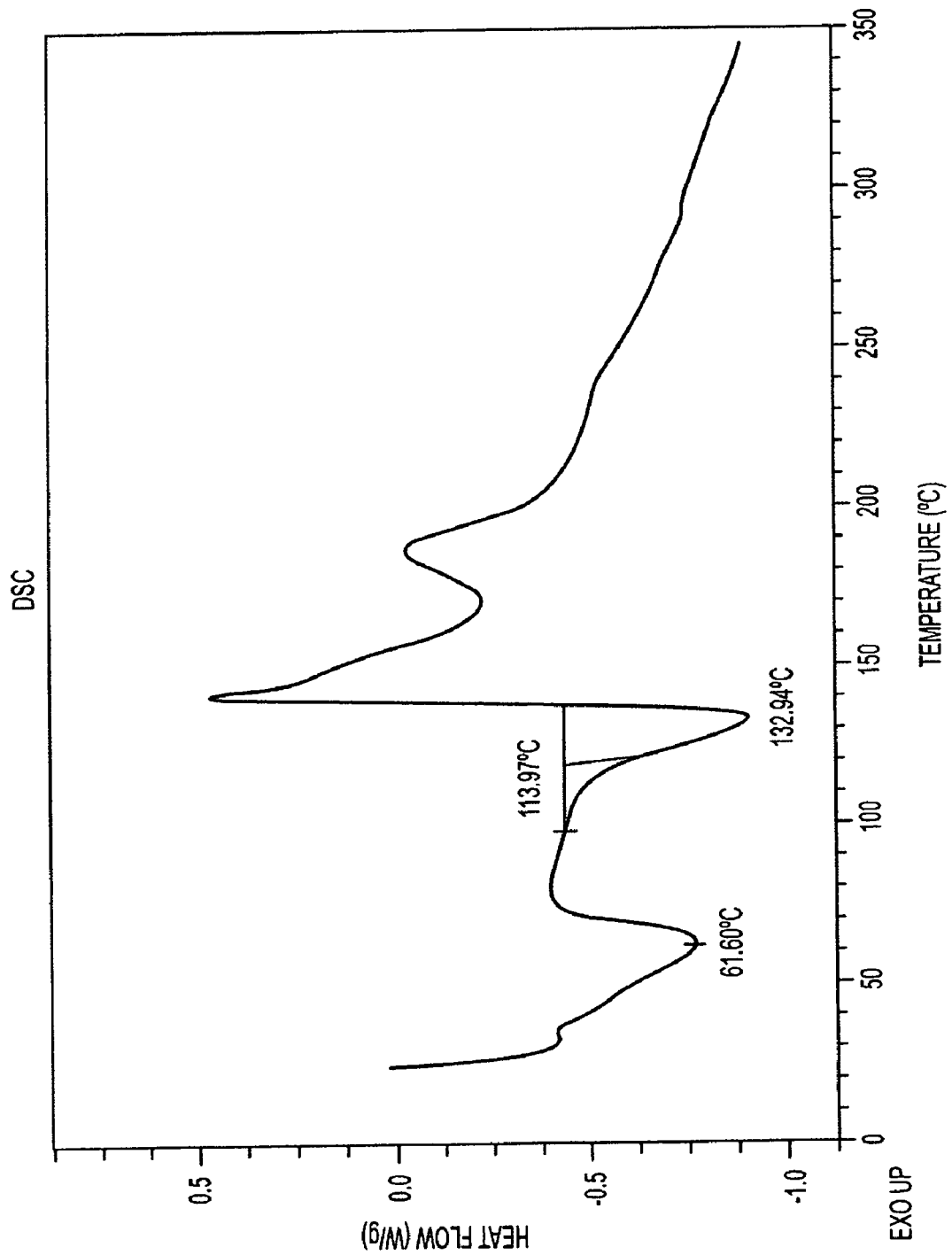
FIG. 16 is the DSC thermogram of crystalline methanol/racemic ilaprazole solvate, Form G.

FIG. 16 is the DSC thermogram of crystalline methanol/racemic ilaprazole solvate, Form G. The DSC thermogram a broad endotherm at about 62° C. and a second endotherm onset occurred at 114° C. (max 133° C.). First endotherm is likely due to desolvation (loss of methanol), while the second endotherm/exotherm is melt/decomposition of the desolvated material.

Figure 17:
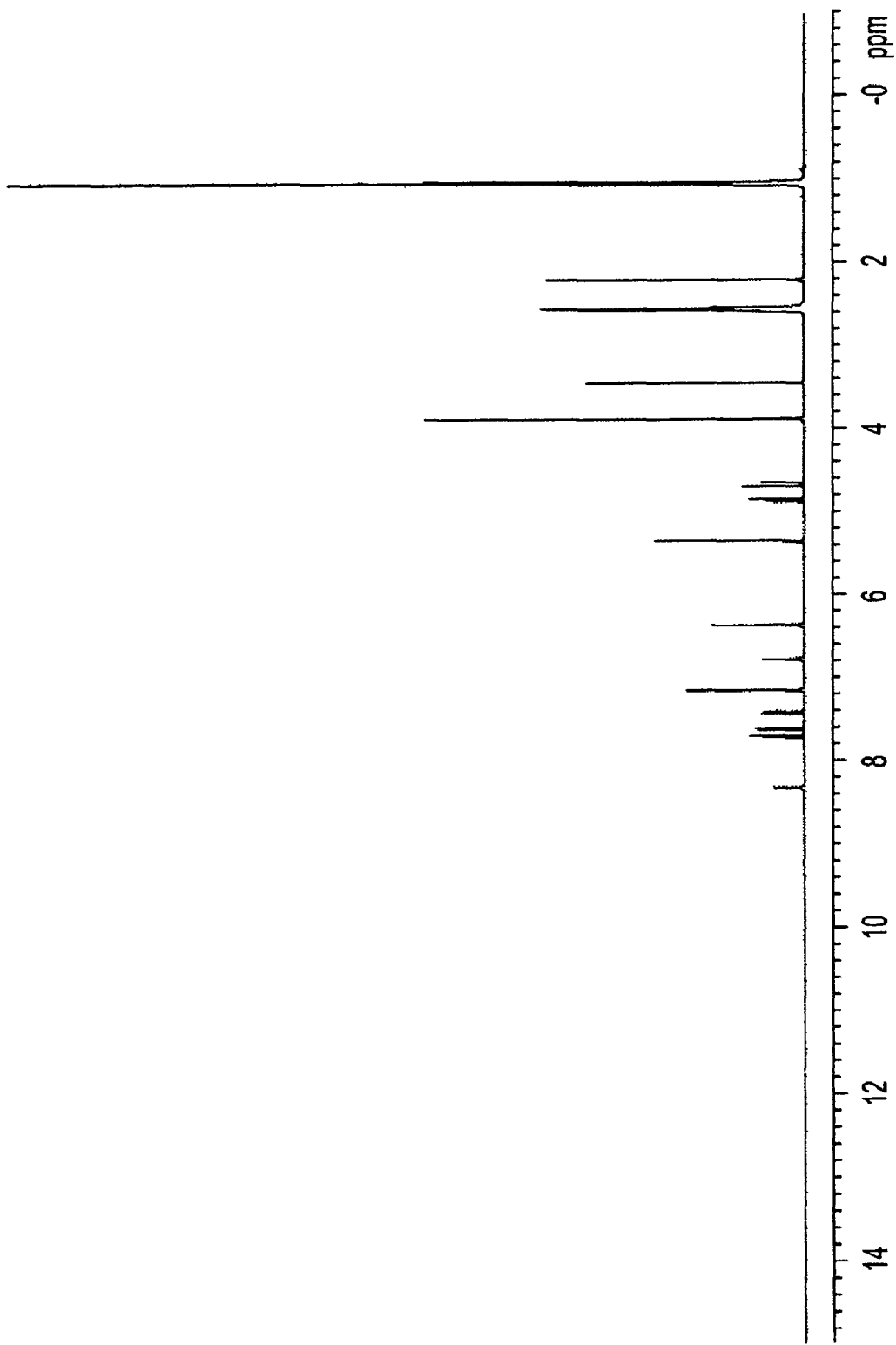
FIG. 17 is the proton NMR spectrum of crystalline methanol/racemic ilaprazole solvate, Form G in $CD_2Cl_2$.

FIG. 17 is the solution state proton NMR spectrum of crystalline methanol/racemic ilaprazole solvate, in CD$_2$Cl$_2$. A peak at approximately 3.4 ppm has been assigned to MeOH and the integration corresponds to ~0.3 moles of MeOH. The peak for the —OH group in MeOH is hidden under the TEA peaks at approximately 1.0 ppm. The spectrum in FIG. 17, therefore, shows Form G to have an approximate 1:0.3 ilaprazole:methanol ratio for this sample. The peaks in the proton NMR spectrum are reported in Table 14. Any peaks near 5.32 ppm are residual protons in the deuterated solvent—not to ilaprazole. Peaks near 1.0 and 2.5 ppm are due to TEA, which is used to stabilize ilaprazole in solution, and not to ilaprazole.

TABLE 14

$^1$H NMR Peaks for Form G
PPM

| |
|---|
| 8.3 |
| 7.7 |
| 7.6 |
| 7.4 |
| 7.1 |
| 6.8 |
| 6.3 |
| 5.3 |
| 4.8 |
| 4.6 |
| 3.9 |
| 3.4 |
| 2.2 |

Figure 18:
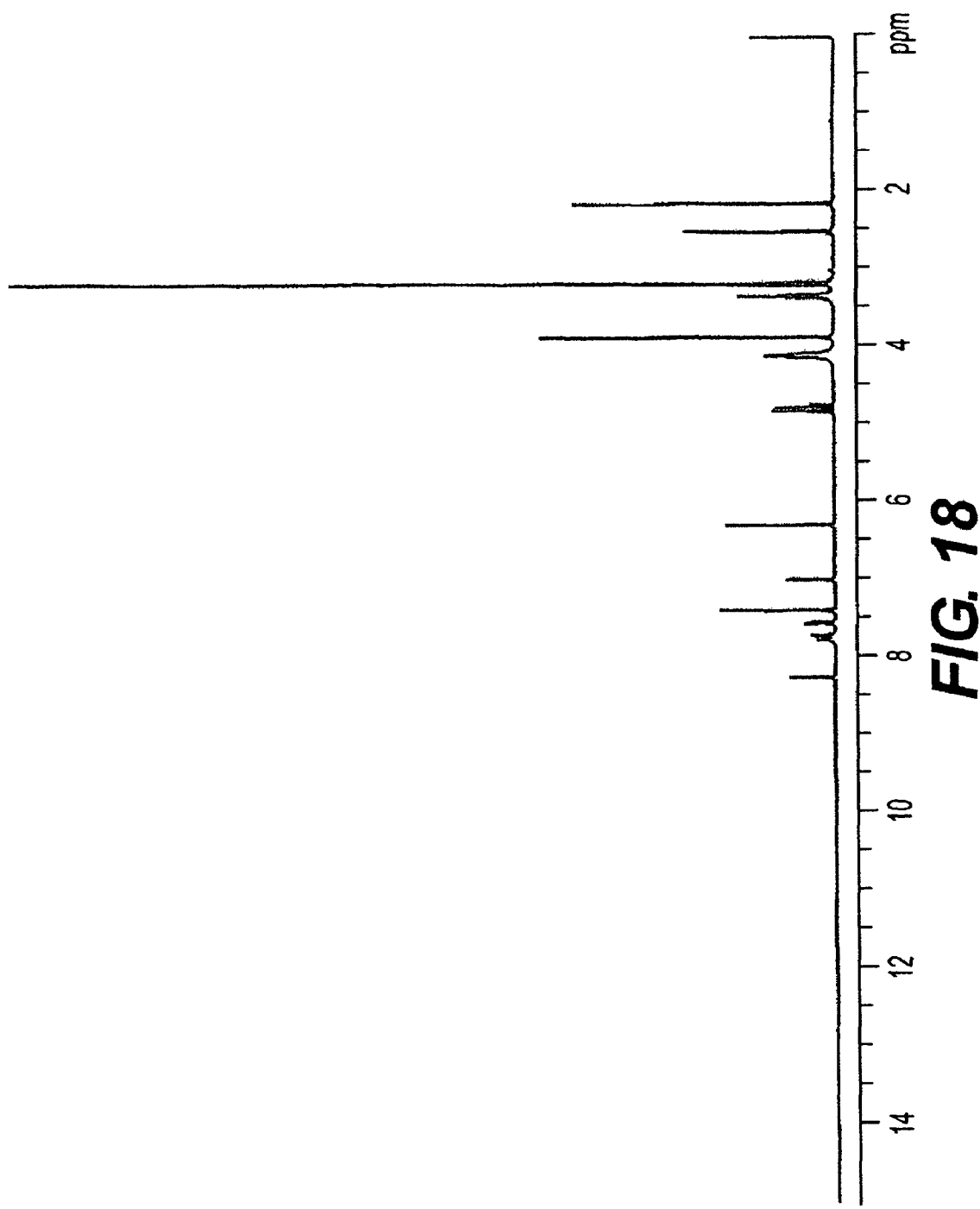
FIG. 18 is the proton NMR spectrum of crystalline methanol/racemic ilaprazole solvate, Form G in DMSO-$d_6$.

FIG. 18 is a different solution state proton NMR spectrum of crystalline methanol/racemic ilaprazole solvate, in DMSO-d$_6$. In this spectra methanol peaks are observed at approximately 3.2 ppm (—CH$_3$), which integrates to ~6.6 moles of methanol. Compared to FIG. 17, the crystalline methanol/racemic ilaprazole solvate in FIG. 18 contains significantly more methanol, indicating that the crystalline methanol/racemic ilaprazole solvate is a variable solvate.

Figure 19:
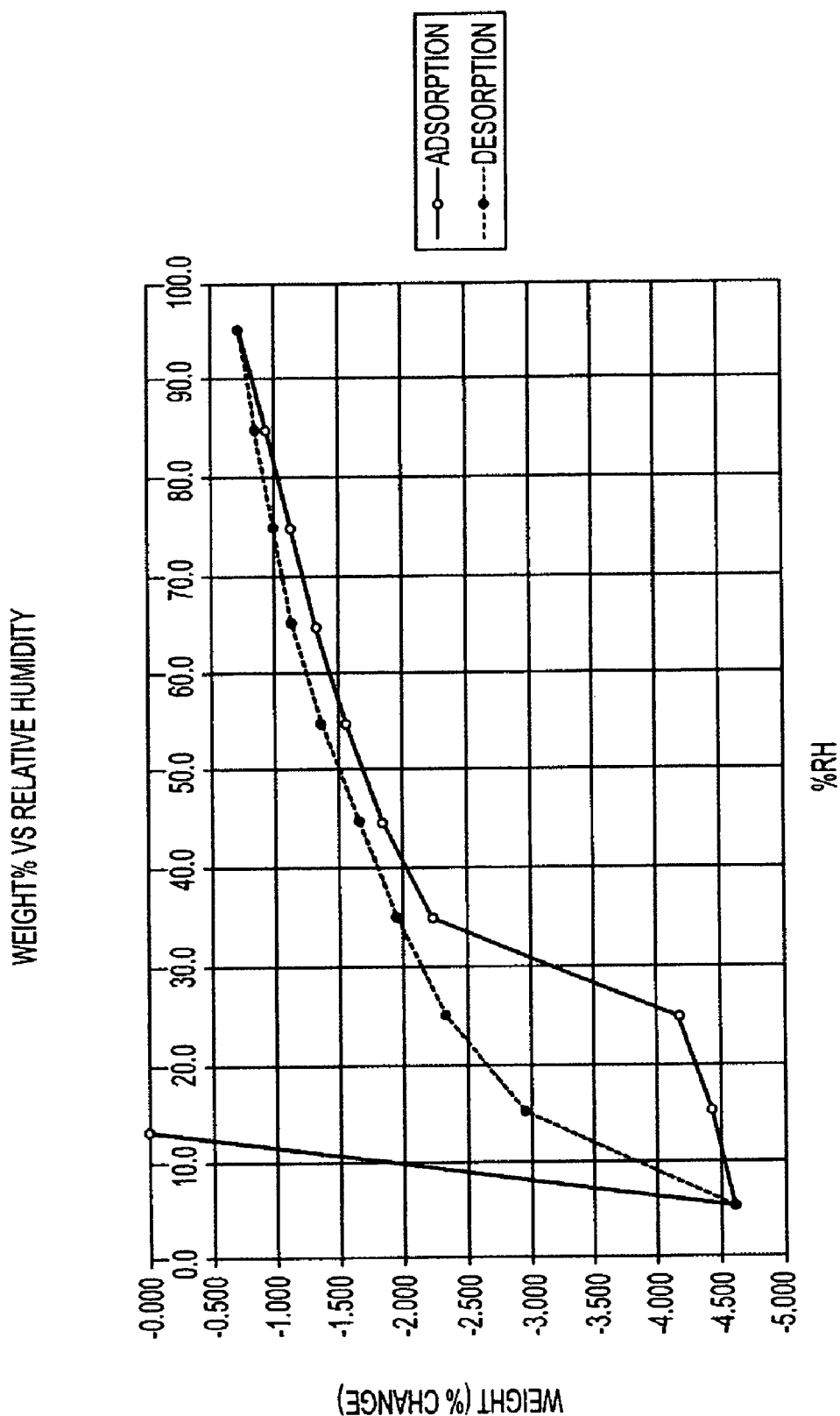
FIG. 19 is the DVS isotherm of crystalline methanol/racemic ilaprazole solvate, Form G.

FIG. 19 is the DVS isotherm of crystalline methanol/racemic ilaprazole solvate, Form G. The DVS isotherm shows an approximate 4.6% weight loss at 5% RH, an approximate 3.9% weight gain from 5 to 95% RH, and an approximate 3.9% weight loss from 95 to 5% RH.

Figure 20:
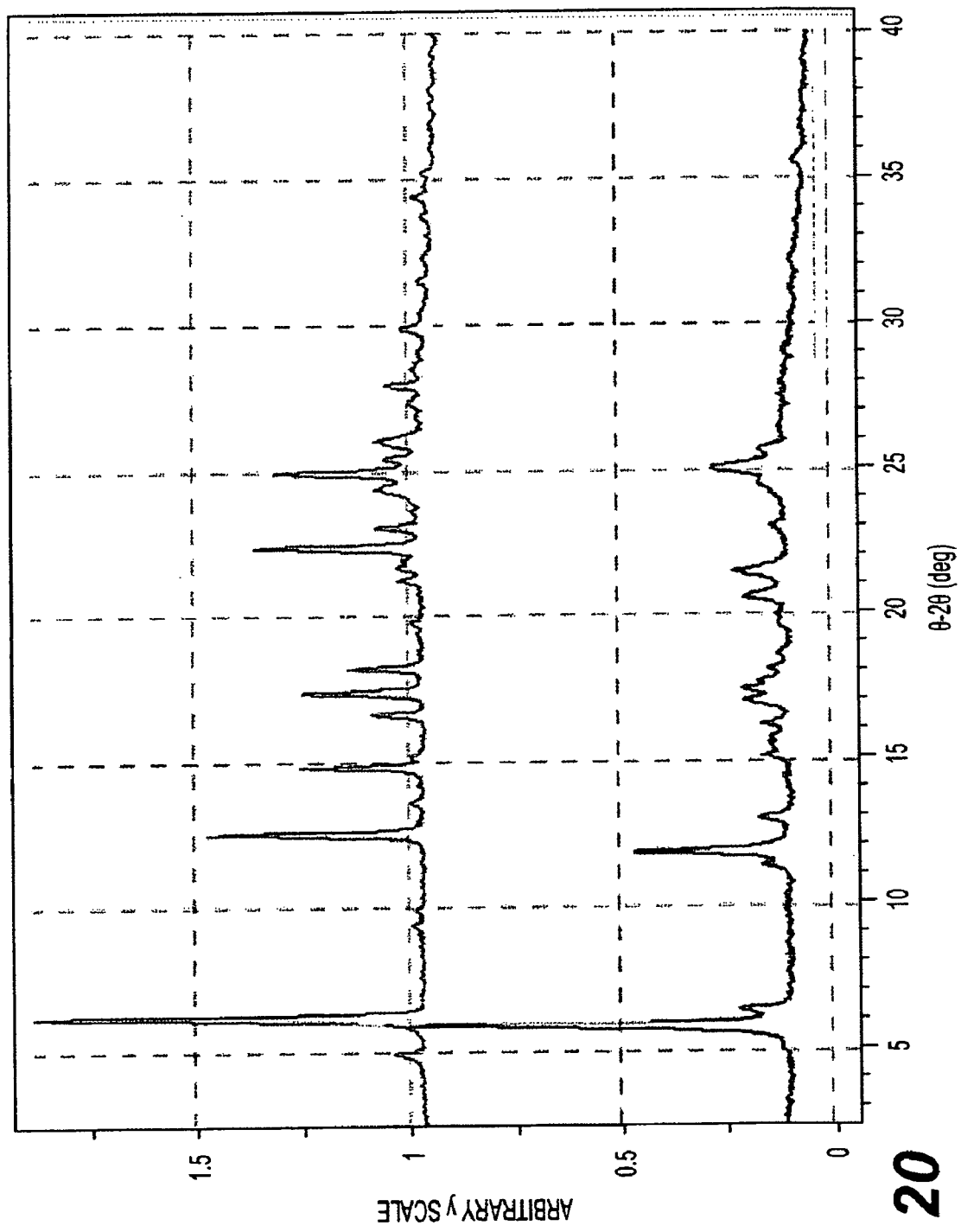
FIG. 20 compares the initial XRPD of crystalline methanol/racemic ilaprazole solvate, Form G, with that of unsolvated crystalline ilaprazole, Form I.

Preparation of unsolvated racemic crystalline ilaprazole, Form I, from crystalline methanol/racemic ilaprazole solvate, Form G: A small spatula full of Form G was placed in a 1 dram glass vial. The open vial was exposed to ambient temperature under vacuum. A white solid resulted approximately 1 day later as unsolvated racemic crystalline ilaprazole, Form I. FIG. 20 shows the XRPD patterns of initial Form G and the resulting Form I.

Example 5

Preparation and Characterization of Crystalline Racemic Ilaprazole Hydrate, Form K A small spatula full of Ilaprazole Form G (see Example 4) was placed in a 1 dram glass vial. The open vial was exposed to ambient temperature and 75% relative humidity. A white solid resulted approximately 1 day later and was identified as crystalline racemic ilaprazole hydrate, Form K. The hydrate is believed to be a mono-hydrate.

Figure 21:
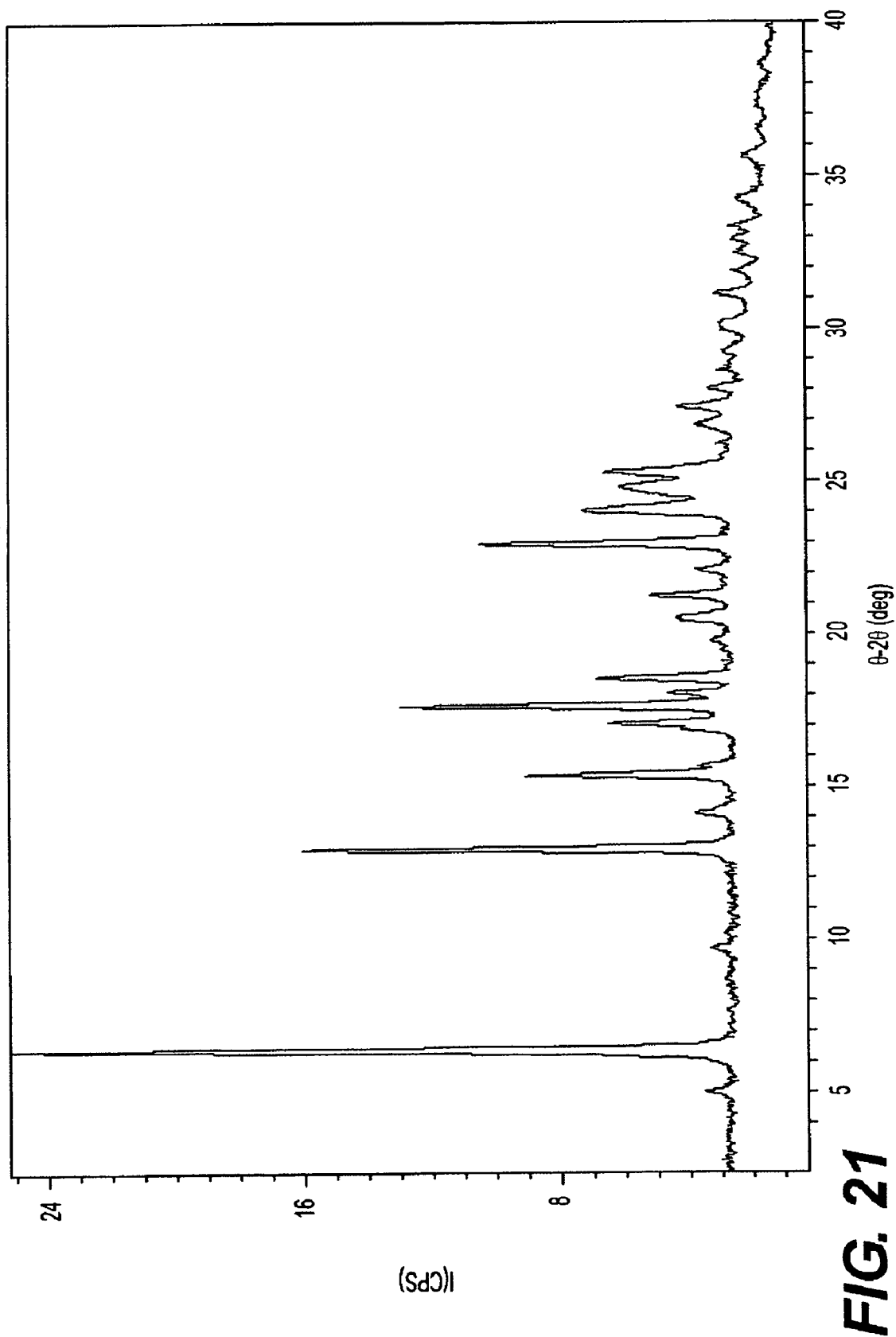
FIG. 21 is the XRPD pattern of crystalline racemic ilaprazole hydrate, Form K.

The XRPD pattern of crystalline racemic ilaprazole hydrate, Form K was obtained using an Inel XRG-3000 diffractometer. The measurement conditions are reported in Table 15. FIG. 21 shows the XRPD pattern for crystalline racemic ilaprazole hydrate, Form K. Table 16 reports the peaks identified in the XRPD pattern.

TABLE 15

| XRPD Processing Conditions for Form K. | |
|---|---|
| Smoothing | [AUTO] |
| smoothing points = | 9 |
| B.G. Subtraction | [AUTO] |
| sampling points = | 11 |
| repeat times = | 30 |
| Ka1-a2 Separate | [MANUAL] |
| Ka1 a2 ratio = | 50.0 (%) |
| Peak Search | [AUTO] |
| differential points = | 9 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 16

| XRPD Peak Positions of Form K | |
|---|---|
| Position (°2θ) | $I/I_o^c$ |
| 5.1 | 4 |
| 6.5 | 100 |
| 9.8 | 3 |
| 13.0 | 61 |
| 14.2 | 5 |
| 15.4 | 29 |
| 15.7 | 5 |
| 16.8 | 3 |
| 17.1 | 18 |
| 17.7 | 47 |
| 18.1 | 9 |
| 18.6 | 19 |
| 20.5 | 7 |
| 21.3 | 11 |
| 22.1 | 5 |
| 23.0 | 36 |
| 23.2 | 4 |
| 24.1 | 21 |
| 24.6 | 9 |
| 24.7 | 13 |
| 24.8 | 15 |
| 25.3 | 18 |
| 26.8 | 5 |
| 27.0 | 4 |
| 27.4 | 9 |
| 28.0 | 5 |
| 30.0 | 3 |
| 30.1 | 4 |
| 31.1 | 6 |
| 31.9 | 3 |
| 33.0 | 4 |
| 33.3 | 4 |
| 34.3 | 3 |
| 35.6 | 3 |

The claimed invention is:

1. A crystalline racemic ilaprazole hydrate, characterized by a powder x-ray diffraction pattern having peaks at 6.5° 2θ±0.2° 2θ and 18.6° 2θ±0.2° 2θ.

2. The crystalline ilaprazole hydrate of claim 1, wherein the crystalline racemic ilaprazole hydrate is crystalline racemic ilaprazole hydrate, Form K.

\* \* \* \* \*